United States Patent
Kim et al.

(10) Patent No.: US 11,059,917 B2
(45) Date of Patent: *Jul. 13, 2021

(54) LIGAND COMPOUND, TRANSITION METAL COMPOUND, AND CATALYST COMPOSITION INCLUDING THE SAME

(71) Applicant: LG Chem, Ltd., Seoul (KR)

(72) Inventors: Dong Eun Kim, Daejeon (KR); Yun Jin Lee, Daejeon (KR); Jung Ho Jun, Daejeon (KR); Seung Hwan Jung, Daejeon (KR); Jin Sam Gong, Daejeon (KR); Choong Hoon Lee, Daejeon (KR)

(73) Assignee: LG Chem, Ltd.

( * ) Notice: Subject to any disclaimer, the term of this patent is extended or adjusted under 35 U.S.C. 154(b) by 175 days.

This patent is subject to a terminal disclaimer.

(21) Appl. No.: 16/311,509

(22) PCT Filed: Nov. 9, 2017

(86) PCT No.: PCT/KR2017/012674
§ 371 (c)(1),
(2) Date: Dec. 19, 2018

(87) PCT Pub. No.: WO2018/088820
PCT Pub. Date: May 17, 2018

(65) Prior Publication Data
US 2019/0233553 A1    Aug. 1, 2019

(30) Foreign Application Priority Data
Nov. 14, 2016 (KR) .................. 10-2016-0151391

(51) Int. Cl.
| | | |
|---|---|---|
| C08F 10/02 | (2006.01) |
| C07D 333/76 | (2006.01) |
| C07F 7/28 | (2006.01) |
| C07F 17/00 | (2006.01) |
| C08F 2/38 | (2006.01) |
| C08F 4/642 | (2006.01) |
| C08F 4/64 | (2006.01) |

(52) U.S. Cl.
CPC ............ *C08F 10/02* (2013.01); *C07D 333/76* (2013.01); *C07F 7/28* (2013.01); *C07F 17/00* (2013.01); *C08F 2/38* (2013.01); *C08F 4/64* (2013.01); *C08F 4/642* (2013.01); *C08F 2420/06* (2013.01)

(58) Field of Classification Search
CPC ............... C08F 10/02; C07D 333/76
See application file for complete search history.

(56) References Cited

U.S. PATENT DOCUMENTS

| | | | |
|---|---|---|---|
| 5,064,802 A | 11/1991 | Stevens et al. | |
| 6,548,686 B2 | 4/2003 | Nabika et al. | |
| 9,822,200 B2 * | 11/2017 | Kim .................. | C08F 4/6592 |
| 2016/0326281 A1 | 11/2016 | Kim et al. | |

FOREIGN PATENT DOCUMENTS

| | | |
|---|---|---|
| CN | 105985383 A | 10/2016 |
| KR | 20160054849 A | 5/2016 |
| WO | 2005118654 A1 | 12/2005 |
| WO | 2009032051 A1 | 3/2009 |

OTHER PUBLICATIONS

Gielens EE, Tiesnitsch JY, Hessen B, Teuben JH. Titanium Hydrocarbyl Complexes with a Linked Cyclopentadienyl-Alkoxide Ancillary Ligand; Participation of the Ligand in an Unusual Activation of a (Trimethylsilyl) methyl Group. Organometallics. Apr. 27, 1998;17(9):1652-4.

Gibson VC, Spitzmesser SK. Advances in non-metallocene olefin polymerization catalysis. Chemical reviews. Jan. 8, 2003;103(1):283-316.

Chen YX, Fu PF, Stern CL, Marks TJ. A Novel Phenolate "Constrained Geometry" Catalyst System. Efficient Synthesis, Structural Characterization, and a-Olefin Polymerization Catalysis. Organometallics. Dec. 23, 1997;16 (26):5958-63.

Christie SD, Man KW, Whitby RJ, Slawin AM. Novel Routes to Bidentate Cyclopentadienyl-Alkoxide Complexes of Titanium: Synthesis of (?5-s-C5R14CHR2CH2CR3R4O) TiCl2. Organometallics. Feb. 1, 1999;18(3):348-59.

Rau A, Schmitz S, Luft G. Synthesis and application in high-pressure polymerization of a titanium complex with a inked cyclopentadienyl-phenoxide ligand. Journal of Organometallic Chemistry. Aug. 25, 2000;608(1-2):71-5.

Turner LE, Thom MG, Fanwick PE, Rothwell IP. Facile resolution of constrained geometry indenyl-phenoxide ligation. Chemical Communications. 2003(9):1034-5.

Zhang Y, Mu Y, Lü C, Li G, Xu J, Zhang Y, Zhu D, Feng S. Constrained geometry tetramethylcyclopentadienyl-phenoxytitanium dichlorides: Template synthesis, structures, and catalytic properties for ethylene polymerization. Organometallics. Feb. 2, 2004;23(3):540-6.

International Search Report for PCT/KR2017/012674 dated Feb. 8, 2018.

* cited by examiner

*Primary Examiner* — Catherine S Branch
(74) *Attorney, Agent, or Firm* — Lerner, David, Littenberg, Krumholz & Mentlik, LLP

(57) ABSTRACT

The present invention relates to a novel ligand compound, a transition metal compound and a catalyst composition including the same. The novel ligand compound and the transition metal compound of the present invention may be useful as a catalyst of polymerization reaction for preparing an olefin-based polymer having a low density. In addition, an olefin polymer which is polymerized using the catalyst composition including the transition metal compound may be used for the manufacture of a product having low melt index (MI) and high molecular weight.

17 Claims, No Drawings

LIGAND COMPOUND, TRANSITION METAL COMPOUND, AND CATALYST COMPOSITION INCLUDING THE SAME

CROSS-REFERENCE TO RELATED APPLICATIONS

This application is a national phase entry under 35 U.S.C. § 371 of International Application No. PCT/KR2017/012674, filed Nov. 9, 2017, which claims priority to Korean Patent Application No. 10-2016-0151391, filed Nov. 14, 2016, the disclosures of which are incorporated herein by reference.

TECHNICAL FIELD

The present invention relates to a novel ligand compound, a transition metal compound, and a catalyst composition including the same.

BACKGROUND ART

[Me$_2$Si(Me$_4$C$_5$)NtBu]TiCl$_2$ (Constrained-Geometry Catalyst, hereinafter, will be abbreviated as CGC) was reported by Dow Co. in the early 1990s (U.S. Pat. No. 5,064,802), and excellent aspects of the CGC in the copolymerization reaction of ethylene and alpha-olefin may be summarized in the following two points when compared to commonly known metallocene catalysts: (1) at a high polymerization temperature, high activity is shown and a polymer having high molecular weight is produced, and (2) the copolymerization degree of alpha-olefin having large steric hindrance such as 1-hexene and 1-octene is excellent. In addition, as various properties of the CGC during performing a polymerization reaction are gradually known, efforts of synthesizing the derivatives thereof and using as a polymerization catalyst has been actively conducted in academy and industry.

As one approach, the synthesis of a metal compound introducing various bridges instead of a silicon bridge and a nitrogen substituent and the polymerization thereof has been conducted. Typical metal compounds known until now are illustrated as Compounds (1) to (4) below (Chem. Rev. 2003, 103, 283).

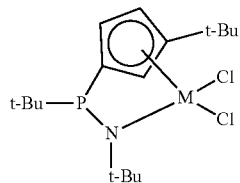
(1)

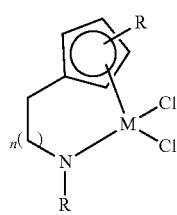
(2)

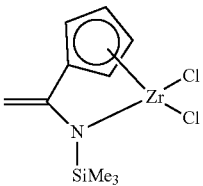
(3)

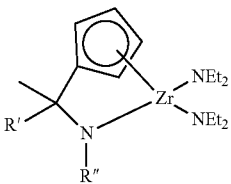
(4)

The above Compounds (1) to (4) introduce a phosphorous bridge (1), an ethylene or propylene bridge (2), a methylidene bridge (3) or a methylene bridge (4) instead of the silicon bridge of a CGC structure. However, improved results on activity, copolymerization performance, etc. could not be obtained by applying an ethylene polymerization or a copolymerization with alpha-olefin when compared to those obtained by applying the CGC.

In addition, as another approach, a lot of compounds composed of an oxido ligand instead of the amido ligand of the CGC have been synthesized, and an attempt on the polymerization using thereof has been conducted to some extent. Examples thereof are summarized in the following.

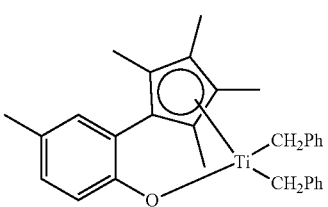
(5)

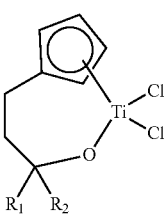
(6)

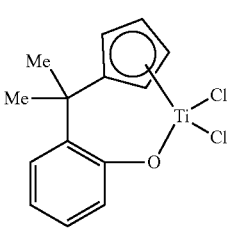
(7)

-continued (8)

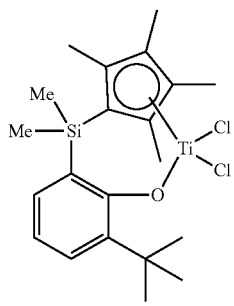

Compound (5) has been reported by T. J. Marks et al. and is characterized in that a cyclopentadiene (Cp) derivative and an oxido ligand are bridged via an ortho-phenylene group (Organometallics 1997, 16, 5958). A compound having the same bridged group and a polymerization using thereof have been reported by Mu et al. (Organometallics 2004, 23, 540). In addition, the bridging of an indenyl ligand and an oxido ligand by the same ortho-phenylene group has been reported by Rothwell et al. (Chem. Commun. 2003, 1034). Compound (6) has been reported by Whitby et al. and is characterized in that a cyclopentadienyl ligand and an oxido ligand are bridged by three carbon atoms (Organometallics 1999, 18, 348). The above catalysts have been reported to show activity in a syndiotactic polystyrene polymerization. Similar compounds have been also reported by Hessen et al. (Organometallics 1998, 17, 1652). Compound (7) has been reported by Rau et al. and is characterized in showing activity in an ethylene polymerization and an ethylene/1-hexene copolymerization at a high temperature and high pressure (210° C., 150 MPa) (J. Organomet. Chem. 2000, 608, 71). In addition, the synthesis of a catalyst (8) having similar structure as that of Compound (7) and a polymerization using the same at a high temperature and a high pressure have been filed by Sumitomo Co. (U.S. Pat. No. 6,548,686). However, not many catalysts among the above attempts are practically applied in commercial plants. Accordingly, a catalyst showing further improved polymerization performance is required, and a simple preparation method of the catalyst is required.

DISCLOSURE OF THE INVENTION

Technical Problem

The first technical problem to be solved by the present invention is to provide a novel transition metal compound.

The second technical problem to be solved by the present invention is to provide a novel ligand compound.

The third technical problem to be solved by the present invention is to provide a catalyst composition comprising the transition metal compound.

Technical Solution

To solve the first technical problem, there is provided in the present invention a transition metal compound represented by the following Formula 1:

[Formula 1]

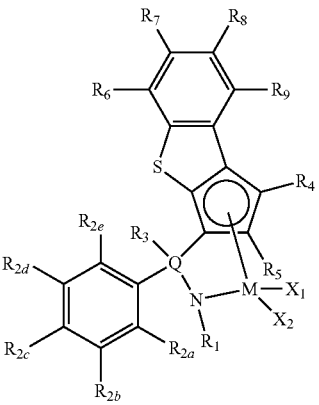

In Formula 1, $R_1$ is hydrogen; alkyl having 1 to 20 carbon atoms; cycloalkyl having 3 to 20 carbon atoms; alkenyl having 2 to carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, $R_{2a}$ to $R_{2e}$ are each independently hydrogen; halogen; alkyl having 1 to 20 carbon atoms; cycloalkyl having 3 to 20 carbon atoms; alkenyl having 2 to 20 carbon atoms; alkoxy having 1 to 20 carbon atoms; or aryl having 6 to 20 carbon atoms, $R_3$ is hydrogen; halogen; alkyl having 1 to 20 carbon atoms; cycloalkyl having 3 to 20 carbon atoms; alkenyl having to 20 carbon atoms; aryl having 6 to 20 carbon atoms; alkylaryl having 6 to 20 carbon atoms; arylalkyl having 7 to carbon atoms; alkyl amido having 1 to 20 carbon atoms; aryl amido having 6 to 20 carbon atoms; alkylidene having 1 to 20 carbon atoms; or phenyl which is substituted with one or more selected from the group consisting of halogen, alkyl having 1 to 20 carbon atoms, cycloalkyl having 3 to 20 carbon atoms, alkenyl having 2 to 20 carbon atoms, alkoxy having 1 to 20 carbon atoms and aryl having 6 to 20 carbon atoms, $R_4$ to $R_9$ are each independently, hydrogen; silyl; alkyl having 1 to 20 carbon atoms; cycloalkyl having 3 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or a metalloid radical of a metal in group 14, which is substituted with hydrocarbyl having 1 to 20 carbon atoms; wherein adjacent two or more of $R_6$ to $R_9$ may be connected to form a ring, Q is Si, C, N, P or S, M is a transition metal in group 4, and $X_1$ and $X_2$ are each independently hydrogen; halogen; alkyl having 1 to 20 carbon atoms; cycloalkyl having 3 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; alkylamino having 1 to 20 carbon atoms; arylamino having 6 to 20 carbon atoms; or alkylidene having 1 to 20 carbon atoms.

To solve the second technical problem, there is provided in the present invention a ligand compound represented by the following Formula 2:

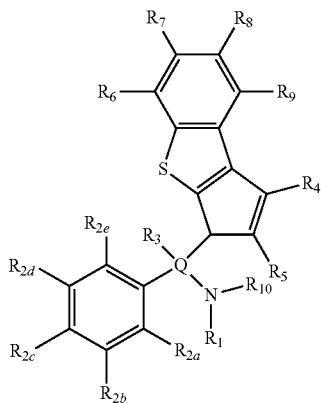

[Formula 2]

In Formula 2, $R_1$ and $R_{10}$ are each independently hydrogen; alkyl having 1 to 20 carbon atoms; cycloalkyl having 3 to 20 carbon atoms; alkenyl having 2 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, $R_{2a}$ to $R_{2e}$ are each independently hydrogen; halogen; alkyl having 1 to 20 carbon atoms; cycloalkyl having 3 to 20 carbon atoms; alkenyl having 2 to 20 carbon atoms; alkoxy having 1 to 20 carbon atoms; or aryl having 6 to 20 carbon atoms, $R_3$ is hydrogen; halogen; alkyl having 1 to 20 carbon atoms; cycloalkyl having 3 to 20 carbon atoms; alkenyl having to 20 carbon atoms; aryl having 6 to 20 carbon atoms; alkylaryl having 6 to 20 carbon atoms; arylalkyl having 7 to carbon atoms; alkyl amido having 1 to 20 carbon atoms; aryl amido having 6 to 20 carbon atoms; alkylidene having 1 to 20 carbon atoms; or phenyl which is substituted with one or more selected from the group consisting of halogen, alkyl having 1 to 20 carbon atoms, cycloalkyl having 3 to 20 carbon atoms, alkenyl having 2 to 20 carbon atoms, alkoxy having 1 to 20 carbon atoms and aryl having 6 to 20 carbon atoms, $R_4$ to $R_9$ are each independently, hydrogen; silyl; alkyl having 1 to 20 carbon atoms; cycloalkyl having 3 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or a metalloid radical of a metal in group 14, which is substituted with hydrocarbyl having 1 to 20 carbon atoms; wherein adjacent two or more of $R_6$ to $R_9$ may be connected to form a ring, and Q is Si, C, N, P or S.

To solve the third technical problem, there is provided in the present invention a catalyst composition comprising the transition metal compound represented by Formula 1.

Advantageous Effects

The novel ligand compound and the transition metal compound of the present invention may be useful as a catalyst of polymerization reaction for preparing an olefin-based polymer having high molecular weight in a low density region, and a polymer having a low melt index (MI) and a low molecular weight may be obtained.

BEST MODE FOR CARRYING OUT THE INVENTION

Hereinafter, the present invention will be described in more detail in order to assist the understanding of the present invention.

It will be understood that words or terms used in the description and claims of the present invention shall not be interpreted as the meaning defined in commonly used dictionaries. It will be further understood that the words or terms should be interpreted as having a meaning that is consistent with their meaning of the technical idea of the invention, based on the principle that an inventor may properly define the meaning of the words or terms to best explain the invention.

The transition metal compound of the present invention is represented by the following Formula 1:

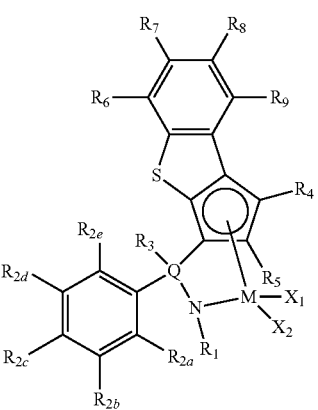

[Formula 1]

In Formula 1, $R_1$ is hydrogen; alkyl having 1 to 20 carbon atoms; cycloalkyl having 3 to 20 carbon atoms; alkenyl having 2 to carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, $R_{2a}$ to $R_{2e}$ are each independently hydrogen; halogen; alkyl having 1 to 20 carbon atoms; cycloalkyl having 3 to 20 carbon atoms; alkenyl having 2 to 20 carbon atoms; alkoxy having 1 to 20 carbon atoms; or aryl having 6 to 20 carbon atoms, $R_3$ is hydrogen; halogen; alkyl having 1 to 20 carbon atoms; cycloalkyl having 3 to 20 carbon atoms; alkenyl having 2 to 20 carbon atoms; aryl having 6 to 20 carbon atoms; alkylaryl having 6 to 20 carbon atoms; arylalkyl having 7 to carbon atoms; alkyl amido having 1 to 20 carbon atoms; aryl amido having 6 to 20 carbon atoms; alkylidene having 1 to 20 carbon atoms; or phenyl which is substituted with one or more selected from the group consisting of halogen, alkyl having 1 to 20 carbon atoms, cycloalkyl having 3 to 20 carbon atoms, alkenyl having 2 to 20 carbon atoms, alkoxy having 1 to 20 carbon atoms and aryl having 6 to 20 carbon atoms, $R_4$ to $R_9$ are each independently, hydrogen; silyl; alkyl having 1 to 20 carbon atoms; cycloalkyl having 3 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or a metalloid radical of a metal in group 14, which is substituted with hydrocarbyl having 1 to 20 carbon atoms; wherein adjacent two or more of $R_6$ to $R_9$ may be connected to form a ring, Q is Si, C, N, P or S, M is a transition metal in group 4, and $X_1$ and $X_2$ are each independently hydrogen; halogen; alkyl having 1 to 20 carbon atoms; cycloalkyl having 3 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; alkylamino having 1 to 20 carbon atoms; arylamino having 6 to 20 carbon atoms; or alkylidene having 1 to 20 carbon atoms.

The transition metal compound of Formula 1 according to the present invention forms a structure in which cyclopentadiene fused with benzothiophene via a ring type bond and an amido group (N—$R_1$) are stably bridged by Q (Si, C, N or P), and a transition metal in group 4 makes a coordination bond.

In applying the catalyst composition for the olefin polymerization, the production of polyolefin with high activity at a high polymerization temperature, a high molecular weight and high copolymerization degree is capable. Particularly, due to the structural characteristics of a catalyst, a large amount of alpha-olefin as well as linear polyethylene with a low density to a degree of 0.850 g/cc to 0.930 g/cc may be introduced, and a polymer (elastomer) in a very low density region such as a density of less than 0.910 g/cc may be prepared.

In the present invention, the term "halogen" means fluorine, chlorine, bromine or iodine unless otherwise noted.

In the present invention, the term "alkyl" means linear, cyclic or branched hydrocarbon residue unless otherwise noted.

In the present invention, the term "cycloalkyl" means cyclic alkyl such as cyclopropyl unless otherwise noted.

In the present invention, the term "aryl" means an aromatic group such as phenyl, naphthyl anthryl, phenanthryl, chrysenyl, and pyrenyl unless otherwise noted.

In the present invention, silyl may be silyl which is substituted with alkyl having 1 to 20 carbon atoms, for example, trimethylsilyl or triethylsilyl.

In the transition metal compound of Formula 1 according to an embodiment of the present invention, $R_1$ may be hydrogen; alkyl having 1 to 20 carbon atoms; cycloalkyl having 3 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, $R_{2a}$ to $R_{2e}$ may be each independently hydrogen; halogen; alkyl having 1 to 12 carbon atoms; cycloalkyl having 3 to 12 carbon atoms; alkenyl having 2 to 12 carbon atoms; alkoxy having 1 to 12 carbon atoms; or phenyl, $R_3$ may be hydrogen; halogen; alkyl having 1 to 12 carbon atoms; cycloalkyl having 3 to 12 carbon atoms; alkenyl having 2 to 12 carbon atoms; aryl having 6 to 20 carbon atoms; alkylaryl having 7 to 13 carbon atoms; arylalkyl having 7 to 13 carbon atoms; or phenyl which is substituted with one or more selected from the group consisting of halogen, alkyl having 1 to 12 carbon atoms, cycloalkyl having 3 to 12 carbon atoms, alkenyl having 2 to 12 carbon atoms, alkoxy having 1 to 12 carbon atoms and phenyl, $R_4$ to $R_9$ may be each independently hydrogen; alkyl having 1 to 20 carbon atoms; cycloalkyl having 3 to 20 carbon atoms; aryl having 6 to 20 carbon atoms; alkylaryl having 7 to 20 carbon atoms; or arylalkyl having 7 to 20 carbon atoms, adjacent two or more of $R_6$ to $R_9$ may be connected to form an aliphatic ring having 5 to 20 carbon atoms or an aromatic ring having 6 to 20 carbon atoms; wherein the aliphatic ring or the aromatic ring may be substituted with halogen, alkyl having 1 to 20 carbon atoms, alkenyl having 2 to 12 carbon atoms, or aryl having 6 to 12 carbon atoms, Q may be Si, M may be Ti, and $X_1$ and $X_2$ may be each independently hydrogen; halogen; alkyl having 1 to 12 carbon atoms; cycloalkyl having 3 to 12 carbon atoms; alkenyl having 2 to 12 carbon atoms; aryl having 6 to 12 carbon atoms; alkylaryl having 7 to 13 carbon atoms; arylalkyl having 7 to 13 carbon atoms; alkylamino having 1 to 13 carbon atoms; arylamino having 6 to 12 carbon atoms; or alkylidene having 1 to 12 carbon atoms.

In addition, in the transition metal compound of Formula 1 according to another embodiment of the present invention, $R_1$ may be hydrogen; alkyl having 1 to 12 carbon atoms; cycloalkyl having 3 to 12 carbon atoms; alkoxy having 1 to 12 carbon atoms; aryl having 6 to 12 carbon atoms; arylalkoxy having 7 to 13 carbon atoms; alkylaryl having 7 to 13 carbon atoms; or arylalkyl having 7 to 13 carbon atoms, $R_{2a}$ to $R_{2e}$ may be each independently hydrogen; halogen; alkyl having 1 to 12 carbon atoms; cycloalkyl having 3 to 12 carbon atoms; alkenyl having 2 to 12 carbon atoms; alkoxy having 1 to 12 carbon atoms; or phenyl, $R_3$ may be hydrogen; halogen; alkyl having 1 to 12 carbon atoms; cycloalkyl having 3 to 12 carbon atoms; alkenyl having 2 to 12 carbon atoms; alkylaryl having 7 to 13 carbon atoms; arylalkyl having 7 to 13 carbon atoms; phenyl; or phenyl which is substituted with one or more selected from the group consisting of halogen, alkyl having 1 to 12 carbon atoms, cycloalkyl having 3 to 12 carbon atoms, alkenyl having 2 to 12 carbon atoms, alkoxy having 1 to 12 carbon atoms and phenyl, $R_4$ to $R_9$ may be each independently, hydrogen; alkyl having 1 to 12 carbon atoms; cycloalkyl having 3 to 12 carbon atoms; aryl having 6 to 12 carbon atoms; alkylaryl having 7 to 13 carbon atoms; or arylalkyl having 7 to 13 carbon atoms, adjacent two or more of $R_6$ to $R_9$ may be connected to form an aliphatic ring having 5 to 12 carbon atoms or an aromatic ring having 6 to 12 carbon atoms; where the aliphatic ring or the aromatic ring may be substituted with halogen, alkyl having 1 to 12 carbon atoms, alkenyl having 2 to 12 carbon atoms, or aryl having 6 to 12 carbon atoms, Q may be Si, M may be Ti, and $X_1$ and $X_2$ may be each independently hydrogen; halogen; alkyl having 1 to 12 carbon atoms; or alkenyl having 2 to 12 carbon atoms.

In addition, in the transition metal compound of Formula 1 according to further another embodiment of the present invention, $R_1$ may be hydrogen or alkyl having 1 to 12 carbon atoms, $R_{2a}$ to $R_{2e}$ may be each independently hydrogen; alkyl having 1 to 12 carbon atoms; or alkoxy having 1 to 12 carbon atoms, $R_3$ may be hydrogen; alkyl having 1 to 12 carbon atoms; or phenyl, $R_4$ and $R_5$ may be each independently hydrogen; or alkyl having 1 to 12 carbon atoms, $R_6$ to $R_9$ may be each independently hydrogen or methyl, Q may be Si, M may be Ti, and $X_1$ and $X_2$ may be each independently hydrogen or alkyl having 1 to 12 carbon atoms.

The compound represented by Formula 1 may particularly be one of the compounds represented by the following Formulae 1-1 to 1-10:
[Formula 1-1]
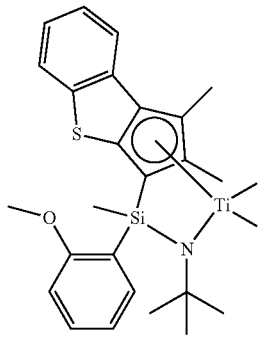
[Formula 1-2]
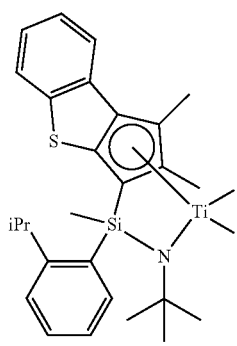
[Formula 1-3]
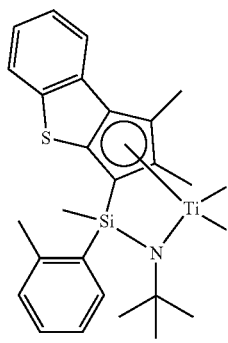
[Formula 1-4]
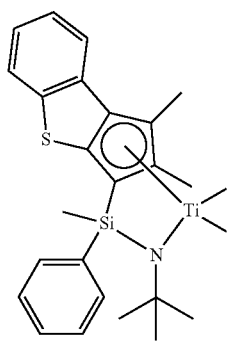
[Formula 1-5]
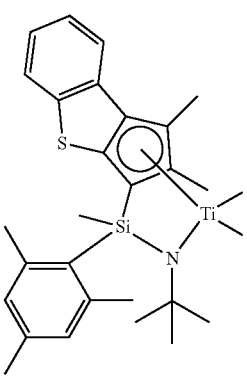
[Formula 1-6]
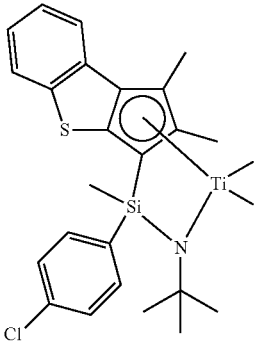
[Formula 1-7]
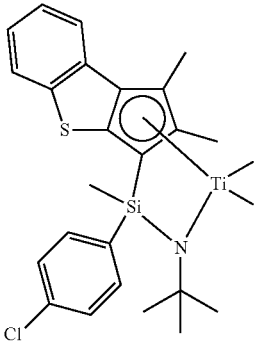
[Formula 1-8]
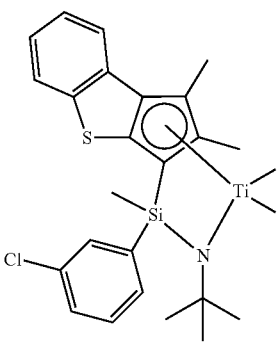

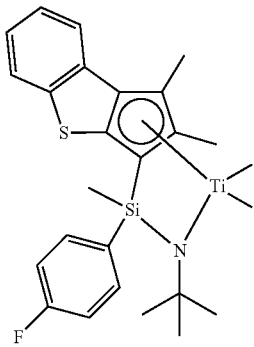

[Formula 1-9]

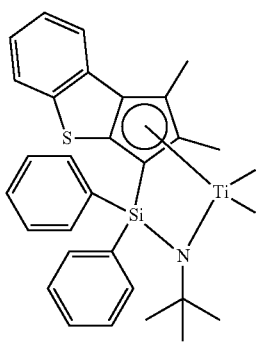

[Formula 1-10]

In addition, to accomplish the above-described second task, there is provided in the present invention a ligand compound represented by the following Formula 2:

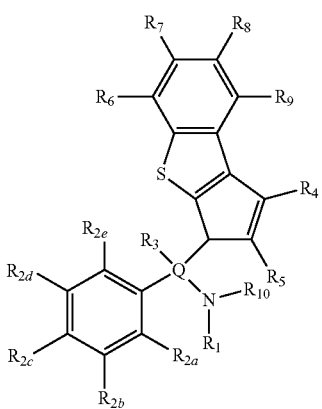

[Formula 2]

In Formula 2, $R_1$ and $R_{10}$ are each independently hydrogen; alkyl having 1 to 20 carbon atoms; cycloalkyl having 3 to 20 carbon atoms; alkenyl having 2 to 20 carbon atoms; alkoxy having 1 to 20 carbon atoms; aryl having 6 to 20 carbon atoms; arylalkoxy having 7 to 20 carbon atoms; alkylaryl having 7 to 20 carbon atoms; or arylalkyl having 7 to 20 carbon atoms, $R_{2a}$ to $R_{2e}$ are each independently hydrogen; halogen; alkyl having 1 to 20 carbon atoms; cycloalkyl having 3 to 20 carbon atoms; alkenyl having 2 to 20 carbon atoms; alkoxy having 1 to 20 carbon atoms; or aryl having 6 to 20 carbon atoms, $R_3$ is hydrogen; halogen; alkyl having 1 to 20 carbon atoms; cycloalkyl having 3 to 20 carbon atoms; alkenyl having to 20 carbon atoms; aryl having 6 to 20 carbon atoms; alkylaryl having 6 to 20 carbon atoms; arylalkyl having 7 to carbon atoms; alkyl amido having 1 to 20 carbon atoms; aryl amido having 6 to 20 carbon atoms; alkylidene having 1 to 20 carbon atoms; or phenyl which is substituted with one or more selected from the group consisting of halogen, alkyl having 1 to 20 carbon atoms, cycloalkyl having 3 to 20 carbon atoms, alkenyl having 2 to 20 carbon atoms, alkoxy having 1 to 20 carbon atoms and aryl having 6 to 20 carbon atoms, $R_4$ to $R_9$ are each independently, hydrogen; silyl; alkyl having 1 to 20 carbon atoms; cycloalkyl having 3 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or a metalloid radical of a metal in group 14, which is substituted with hydrocarbyl having 1 to 20 carbon atoms; wherein adjacent two or more of $R_6$ to $R_9$ may be connected to form a ring, and Q is Si, C, N, P or S.

The ligand compound of Formula 2 described in this disclosure forms a structure in which cyclopentadiene fused with benzothiophene via a ring type bond and an amido group (N—$R_1$) are stably bridged by Q (Si, C, N or P).

In the ligand compound, the definition of $R_1$ to $R_9$ of the compound represented by Formula 2 may be the same as that of the compound represented by Formula 1 which is a transition compound.

In addition, in the ligand compound of Formula 2 according to another embodiment of the present invention, $R_1$, $R_{10}$ and $R_{11}$ may be each independently hydrogen; alkyl having 1 to 12 carbon atoms; cycloalkyl having 3 to 12 carbon atoms; alkoxy having 1 to 12 carbon atoms; aryl having 6 to 12 carbon atoms; arylalkoxy having 7 to 13 carbon atoms; alkylaryl having 7 to 13 carbon atoms; or arylalkyl having 7 to 13 carbon atoms, $R_{2a}$ to $R_{2e}$ may be each independently hydrogen; halogen; alkyl having 1 to 12 carbon atoms; cycloalkyl having 3 to 12 carbon atoms; alkenyl having 2 to 12 carbon atoms; alkoxy having 1 to 12 carbon atoms; or phenyl, $R_3$ may be hydrogen; halogen; alkyl having 1 to 12 carbon atoms; cycloalkyl having 3 to 12 carbon atoms; alkenyl having 2 to 12 carbon atoms; alkylaryl having 7 to 13 carbon atoms; arylalkyl having 7 to 13 carbon atoms; phenyl; or phenyl which is substituted with one or more selected from the group consisting of halogen, alkyl having 1 to 12 carbon atoms, cycloalkyl having 3 to 12 carbon atoms, alkenyl having 2 to 12 carbon atoms, alkoxy having 1 to 12 carbon atoms and phenyl, $R_4$ to $R_9$ may be each independently, hydrogen; alkyl having 1 to 12 carbon atoms; cycloalkyl having 3 to 12 carbon atoms; aryl having 6 to 12 carbon atoms; alkylaryl having 7 to 13 carbon atoms; or arylalkyl having 7 to 13 carbon atoms, adjacent two or more of $R_6$ to $R_9$ may be connected to form an aliphatic ring having 5 to 12 carbon atoms or an aromatic ring having 6 to 12 carbon atoms; wherein the aliphatic ring or the aromatic ring may be substituted with halogen, alkyl having 1 to 12 carbon atoms, alkenyl having 2 to 12 carbon atoms, or aryl having 6 to 12 carbon atoms, and Q may be Si.

In addition, in Formula 2, $R_{10}$ and $R_{11}$ may be each independently hydrogen; alkyl having 1 to 12 carbon atoms; cycloalkyl having 3 to 12 carbon atoms; aryl having 6 to 12 carbon atoms; or alkylaryl having 6 to 12 carbon atoms, particularly, hydrogen.

The compound represented by Formula 2 may be one of the compounds represented by the following Formulae 2-1 to 2-10:
[Formula 2-1]
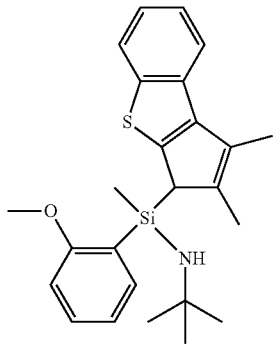
[Formula 2-2]
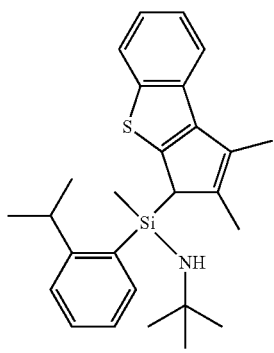
[Formula 2-3]
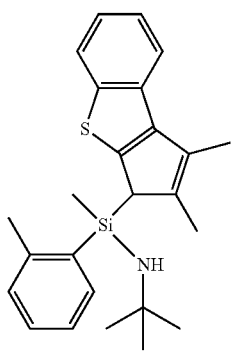
[Formula 2-4]
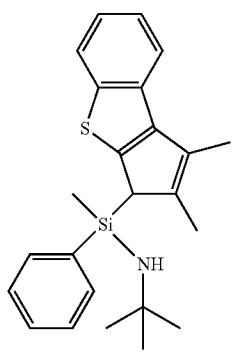
[Formula 2-5]
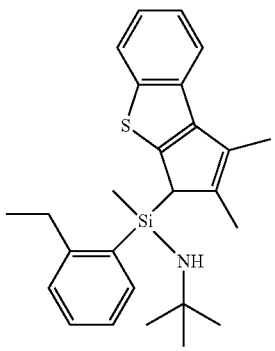
[Formula 2-6]
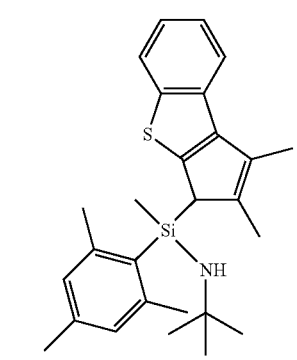
[Formula 2-7]
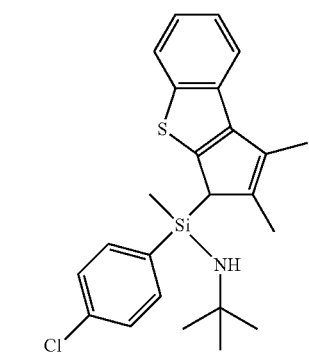
[Formula 2-8]
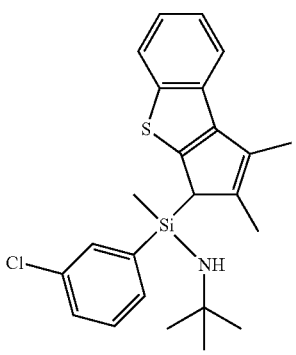

-continued

[Formula 2-9]

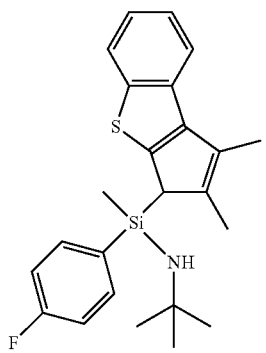

[Formula 2-10]

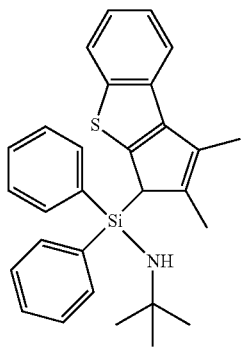

The transition metal compound of Formula 1 and the ligand compound of Formula 2 may particularly be used for the preparation of a catalyst for polymerizing olefin monomers, but may be applied to other all fields in which the transition metal compound may be used, without limitation.

The ligand compound represented by Formula 2 of the present invention may be prepared, for example, by the following Reaction 1:

[Reaction 1]

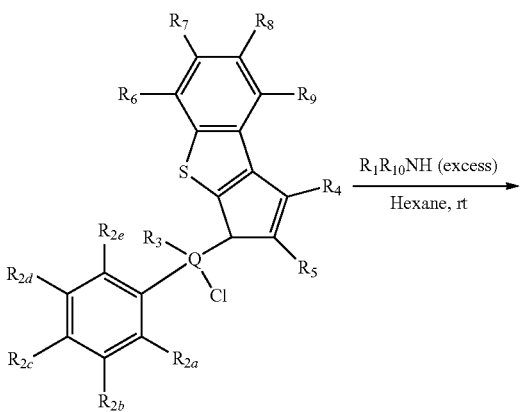

-continued

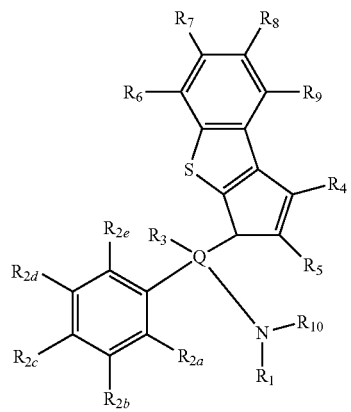

In Reaction 1, $R_1$ to $R_{10}$ and Q are the same as defined in Formula 2.

Particularly, the ligand compound of Formula 2 may be prepared by the following steps a) and b):

a) a step of reacting a compound represented by [Formula 4] below and a compound represented by [Formula 5] below to prepare a compound represented by [Formula 3] below; and b) a step of reacting the compound represented by [Formula 3] below with a compound represented by [Formula 6] below to prepare a compound represented by [Formula 2] below:

[Formula 4]

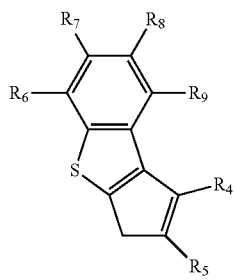

[Formula 5]

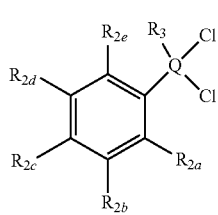

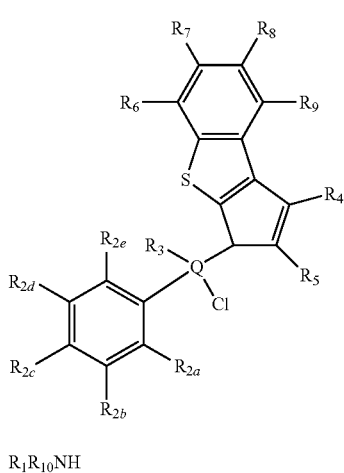

$R_1R_{10}NH$

[Formula 6]

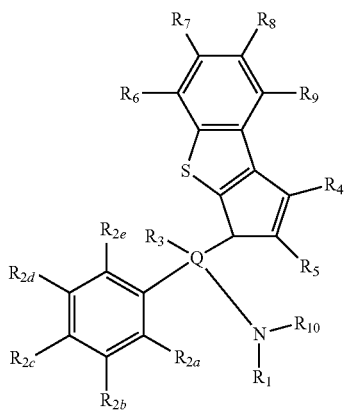

[Formula 2]

In the above formulae, $R_1$ to $R_{10}$ and Q are the same as defined in Formula 2.

The compound represented by Formula 4 may be prepared by the following Reaction 2:

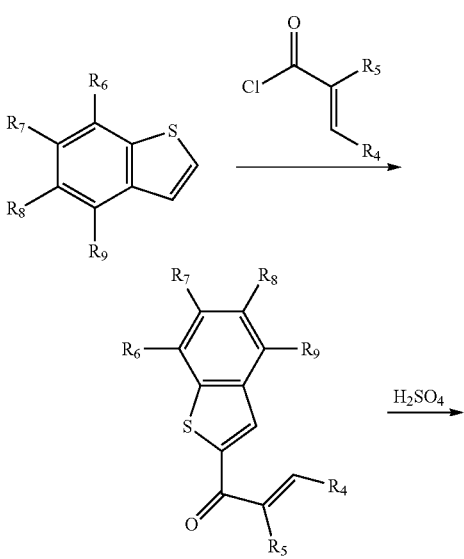

[Formula 3]

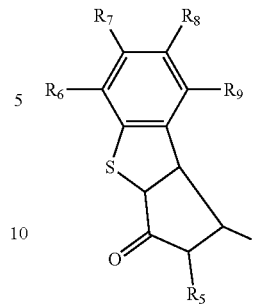

Formula 4

In Reaction 2, $R_4$ to $R_9$ are the same as defined in Formula 1 or Formula 2.

The transition metal compound represented by Formula 1 may be prepared via the following Reaction 3 using a ligand compound represented by Formula 2:

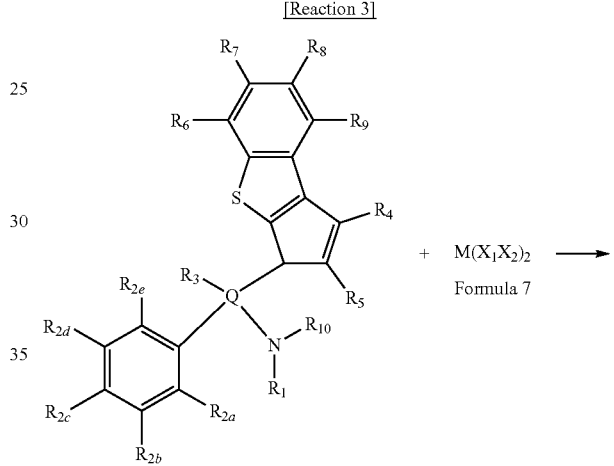

Formula 1

In the above reaction, $R_1$ to $R_{10}$, Q, M, $X_1$ and $X_2$ are the same as defined in Formula 1 or Formula 2.

According to an embodiment of the present invention, the transition metal compound represented by Formula 1 may have a structure in which a transition metal in group 4 makes a coordination bond with the compound represented by Formula 2 as a ligand.

Particularly, as shown in Reaction 3, by reacting the compound represented by Formula 2 with the compound represented by Formula 7 which is a metal precursor and an organolithium compound, the transition metal compound of Formula 1 in which a transition metal in group 4 makes a coordination bond with the compound represented by Formula 2 as a ligand, may be obtained.

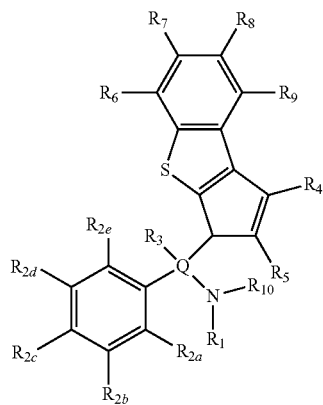

[Formula 2]

$M(X_1X_2)_2$ [Formula 7]

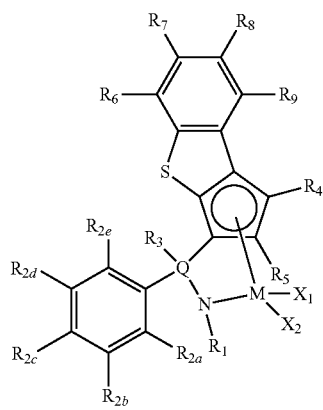

[Formula 1]

In the above formulae, $R_1$ to $R_{10}$, Q, M, $X_1$ and $X_2$ are the same as defined in Formula 1.

In Reaction 3, the organolithium compound may be, for example, one or more selected from the group consisting of n-butyllithium, sec-butyllithium, methyllithium, ethyllithium, isopropyllithium, cyclohexyllithium, allyllithium, vinyllithium, phenyllithium and benzyllithium.

The compound represented by Formula 2 and the compound represented by Formula 5 may preferably be mixed in a molar ratio of 1:0.8 to 1:1.5, particularly, 1:1.0 to 1:1.1.

In addition, the organolithium compound may be used in an amount of 180 parts by weight to 250 parts by weight based on 100 parts by weight of the compound represented by Formula 2.

In the preparation method according to an embodiment of the present invention, the reaction may be performed in a temperature range of −80° C. to 140° C. for 1 to 48 hours.

According to an embodiment of the present invention, the compound represented by Formula 3 and the compound represented by Formula 6 may be used in a molar ratio of 1:0.8 to 1:5.0, particularly, 1:0.9 to 1:4.5, more particularly, 1:1 to 1:4.0.

In addition, according to an embodiment of the present invention, the compound represented by Formula 4 and the compound represented by Formula 5 may be used in a molar ratio of 1:0.8 to 1:5.0, particularly, 1:0.9 to 1:4.0, more particularly, 1:1 to 1:3.0.

In addition, the reaction may be performed in a temperature range of −80° C. to 140° C. for 1 to 48 hours.

The present invention also provides a catalyst composition including the compound of Formula 1.

The catalyst composition may further include a cocatalyst. The cocatalyst may be any one known in this art.

For example, the catalyst composition may further include at least one of the following Formulae 8 to 10 as a cocatalyst:

—[Al($R_{13}$)—O]$_a$— [Formula 8]

In the above formula, each $R_{13}$ is independently a halogen radical; a hydrocarbyl radical of 1 to 20 carbon atoms; or a halogen substituted hydrocarbyl radical of 1 to 20 carbon atoms; and a is an integer of 2 or more;

D($R_{13}$)$_3$ [Formula 9]

In the above formula, D is aluminum or boron; each $R_{13}$ is independently the same as defined above; and

[L-H]$^+$[Z(A)$_4$]$^-$ or

[L]$^+$[Z(A)$_4$] [Formula 10]

In the above formula, L is a neutral or a cationic Lewis acid; H is a hydrogen atom; Z is an element in group 13; and each A is independently aryl having 6 to 20 carbon atoms or alkyl having 1 to 20 carbon atoms, where at least one hydrogen atom may be substituted with a substituent; wherein the substituent is halogen, hydrocarbyl having 1 to 20 carbon atoms, alkoxy having 1 to 20 carbon atoms or aryloxy of 6 to 20 carbon atoms.

As a preparation method of the catalyst composition, there is provided a first preparation method including a step of obtaining a mixture by contacting the transition metal compound represented by Formula 1 with the compound represented by Formula 8 or Formula 9; and a step of adding the compound represented by Formula 10 to the mixture.

Also, there is provided a second preparation method of the catalyst composition by contacting the transition metal compound represented by Formula 1 and the compound represented by Formula 10.

In the first method of the preparation methods of the catalyst composition, the molar ratio of the compound represented by Formula 8 or Formula 9 with respect to the transition metal compound represented by Formula 1 may be, respectively, from 1:2 to 1:5,000, particularly, from 1:10 to 1:1,000, more particularly, from 1:20 to 1:500.

Meanwhile, the molar ratio of the compound represented by Formula 10 with respect to the transition metal compound represented by Formula 1 may be from 1:1 to 1:25, particularly, from 1:1 to 1:10, more particularly, from 1:1 to 1:5.

If the molar ratio of the compound represented by Formula 8 or Formula 9 with respect to the transition metal compound represented by Formula 1 is less than 1:2, the amount of an alkylating agent is very small, and the alkylation of the metal compound may be incompletely achieved, and if the molar ratio is greater than 1:5,000, alkylation of the metal compound may be performed, but side reactions between the remaining excessive amount of alkylating agent and the activating agent of Formula 10 may be performed, and the activation of the alkylated metal compound may be incompletely achieved. In addition, if the molar ratio of the compound represented by Formula 10 with respect to the transition metal compound represented by Formula 2 is less than 1:1, the amount of the activating agent is relatively small, the activation of the metal compound may be incompletely achieved, and the activity of the catalyst composition may be reduced, and if the molar ratio is greater than 1:25, the activation of the metal compound may be completely achieved, but the excessive amount of activating agent remained may increase the production cost of the catalyst composition, or the purity of the polymer thus prepared may decrease.

In the second method of the preparation methods of the catalyst composition, the molar ratio of the compound represented by Formula 10 with respect to the transition metal compound of Formula 1 may be from 1:1 to 1:500, particularly, from 1:1 to 1:50, more particularly, from 1:2 to 1:25. If the molar ratio is less than 1:1, the amount of the activating agent is relatively small, the activation of the catalyst composition may be incompletely achieved, and the activity of the catalyst composition thus prepared may be reduced, and if the molar ratio is greater than 1:500, the activation of the metal compound may be completely achieved, but the excessive amount of activating agent remained may increase the unit cost of the catalyst composition, or the purity of the polymer thus prepared may decrease.

As the reaction solvent used during the preparation of the composition, a hydrocarbon solvent such as pentane, hexane, and heptane, or an aromatic solvent such as benzene, and toluene may be used, but the present invention is not limited thereto, and all solvents used in this field may be used.

In addition, the transition metal compound of Formula 1 and the cocatalyst may be used in a supported type by a support. Silica or alumina may be used as the support.

The compound represented by Formula 8 is not specifically limited only if alkylaluminoxane is used. Particular examples thereof may include methylaluminoxane, ethylaluminoxane, isobutylaluminoxane, butylaluminoxane, etc., more particularly, methylaluminoxane.

The compound represented by Formula 9 is not specifically limited, and particular examples thereof may include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, etc., and more particularly, selected from trimethylaluminum, triethylaluminum, and triisobutylaluminum.

Examples of the compound represented by Formula 10 may include triethylammoniumtetraphenylboron, tributylammoniumtetraphenylboron, trimethylammoniumtetraphenylboron, tripropylammoniumtetraphenylboron, trimethylammoniumtetra(p-tolyl)boron, trimethylammoniumtetra(o, p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra (p-trifluoromethylphenyl)aluminum, tributylammoniumtetrapentafluorophenylaluminum, N,N-diethylaniliniumtetraphenylaluminum, N,N-diethylaniliniumtetraphenylaluminum, N,N-diethylaniliniumtetrapentafluorophenylaluminum, diethylammoniumtetrapentatetraphenylaluminum, triphenylphosphoniumtetraphenylaluminum, trimethylphosphoniumtetraphenylaluminum, triethylammoniumtetraphenylaluminum, tributylammoniumtetraphenylaluminum, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, triphenylcarboniumtetra(p-trifluoromethylphenyl)boron, triphenylcarboniumtetrapentafluorophenylboron, etc.

A polyolefin homopolymer or copolymer may be prepared by contacting a catalyst composition including the transition metal compound of Formula 1; and one or more compounds selected from the compounds represented by Formula 8 to Formula 10, with one or more olefin monomers.

The most particular preparation process using the catalyst composition is a solution process. If the composition is used together with an inorganic support such as silica, it may also be applied to a slurry process or a gas phase process.

In the preparation process, the activating catalyst composition may be injected after being dissolved or diluted in an aliphatic hydrocarbon solvent of 5 to 12 carbon atoms such as pentane, hexane, heptane, nonane, decane and an isomer thereof, an aromatic hydrocarbon solvent such as toluene and benzene, or a hydrocarbon solvent substituted with a chlorine atom such as dichloromethane and chlorobenzene, which are appropriate for an olefin polymerization process. The solvent used may preferably be used after removing a small amount of water or air, which functions as a catalyst poison, by treating with a small amount of alkylaluminum, and may be used by further using a cocatalyst.

The olefin monomer which is polymerizable using the metal compound and the cocatalyst may include, for example, ethylene, an alpha-olefin, a cyclic olefin, etc., and a diene olefin-based monomer, a triene olefin-based monomer, etc. having two or more double bonds may also be polymerized. Particular examples of the monomer may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-icocene, norbornene, norbornadiene, ethylidenenorbornene, phenylnorbornene, vinylnorbornene, dicyclopentadiene, 1,4-butadiene, 1,5-pentadiene, 1,6-hexadiene, styrene, alpha-methylstyrene, divinylbenzene, 3-chloromethylstyrene, etc. Two or more of the monomers may be mixed and copolymerized.

Particularly, in the preparation method of the present invention, the catalyst composition has characteristics of preparing a copolymer having high molecular weight and very low density including a polymer density of 0.89 g/cc or less, in a copolymerization reaction of ethylene and a monomer having large steric hindrance such as 1-octene even at a high reaction temperature of 90° C. or more.

According to an embodiment of the present invention, the polymer prepared by the preparation method of the present invention has a density of less than 0.891 g/cc.

According to an embodiment of the present invention, the polymer prepared by the preparation method of the present invention has a density of 0.88 g/cc or less.

According to an embodiment of the present invention, the polymer prepared by the preparation method of the present invention has a density of less than 0.87 g/cc.

In addition, according to an embodiment of the present invention, if a polymer is formed using the transition metal catalyst of Formula 1, the peak of melting temperature (Tm) may have a single phase or two peaks.

Tm may be obtained by using a differential scanning calorimeter 6000 (DSC) manufactured by PerkinElmer Co. and may be obtained by increasing the polymer temperature to 100 C, maintaining at the temperature for 1 minute, then decreasing the temperature to −100 C, and then, increasing the temperature again and measuring the apex of a DSC curve as a melting point (melting temperature).

According to an embodiment of the present invention, the polymer prepared by the preparation method of the present invention has Tm of 69 or less.

According to an embodiment of the present invention, Tm of the polymer prepared by the preparation method of the present invention may show one peak or two peaks.

According to an embodiment of the present invention, the polymer prepared by the preparation method of the present invention may have melt index (Mi) of less than 4.

According to an embodiment of the present invention, the polymer prepared by the preparation method of the present invention may have melt index (Mi) of 2 or less.

According to an embodiment of the present invention, the polymer prepared by the preparation method of the present invention may have melt index (Mi) of 1 or less.

A polymer having high molecular weight may be produced if the melt index is low and less than 2 according to an embodiment of the present invention, and particularly, the polymer may be useful as a multi-layer film for coating or a car compound, which requires a polymer having high molecular weight.

MODE FOR CARRYING OUT THE INVENTION

Hereinafter, the present invention will be explained more particularly referring to the following examples. However, the examples are for assisting the understanding of the present invention, and the scope of the present invention is not limited thereto.

Synthesis of Ligand and Transition Metal Compounds

Organic reagents and solvents were purchased from Aldrich Co. and used after purifying by a standard method unless otherwise noted. In all steps of syntheses, air and humidity were blocked to increase the reproducibility of experiments.

Preparation of Ligand Compound

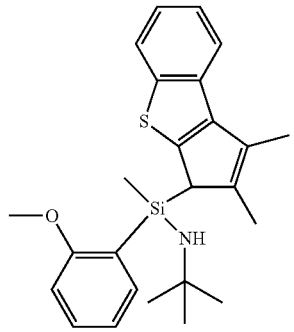

[Formula 2-1]

Synthesis of N-tert-butyl-1-(1,2-dimethyl-3H-benzo[b]cyclopenta[d]thiophene-3-yl)-1,1-(2-methoxyphenyl)(methyl)silaneamine Preparation of chloro-1-(1,2-dimethyl-3H-benzo[b]cyclopenta[d]thiophene-3-yl)-1,1-(2-methoxyphenyl)(methyl)silane To a 100 ml schlenk flask, 3 g (1.1 eq, 14.978 mmol) of 1,2-dimethyl-3H-benzo[b]cyclopenta[d]thiophene and 30 ml of THF were added, and 6.5 ml (1.2 eq, 16.339 mmol, 2.5 M in hexane) of n-BuLi was added thereto dropwisely at −30° C., followed by stirring at room temperature overnight. The THF solution of Li-complex thus stirred was injected into a schlenk flask containing 1.1 g (1.0 eq, 4.99 mmol) of dichloro(2-methoxyphenyl)(methyl)silane and 25 ml of THF at −78° C. by cannulation, followed by stirring at room temperature overnight. After stirring, the reaction mixture was vacuum dried, extracted with 50 ml of hexane, vacuum dried again, and washed with hexane to obtain 1.83 mg of an ivory solid (95%, dr=1:1).

Preparation of N-tert-butyl-1-(1,2-dimethyl-3H-benzo[b]cyclopenta[d]thiophene-3-yl)-1,1-(2-methoxyphenyl)(methyl)silanamine Under a glove box, 314 mg of chloro-1-(1,2-dimethyl-3H-benzo[b]cyclopenta[d]thiophene-3-yl)-1,1-(2-methoxyphenyl)(methyl)silane was weight and injected into a 50 ml vial, and 4 ml of hexane was injected thereto. At room temperature, tBuNH$_2$ (8 eq, 342 μl) was injected, and then reacted at room temperature for 2 days. After finishing the reaction, hexane was removed, and extraction with hexane was performed. After drying solvents, 162.3 mg of a yellow solid was obtained (47%, dr=1:1).

$^1$H-NMR (CDCl$_2$, 500 MHz): δ 7.99 (d, 1H), 7.89 (d, 1H), 7.67 (t, 2H), 7.54 (d, 1H), 7.52 (t, 1H), 7.48 (t, 1H), 7.24 (d, 2H), 7.07 (t, 2H), 7.01 (t, 1H), 6.94 (d, 1H), 6.90 (t, 1H), 6.59 (d, 1H), 6.55 (d, 1H), 4.04 (s, 1H), 4.02 (s, 1H), 3.32 (s, 6H), 2.27 (s, 3H), 2.24 (s, 3H), 1.81 (s, 3H), 1.72 (s, 3H), 1.09 (s, 9H), 1.01 (s, 9H), 0.30 (s, 3H), 0.15 (s, 3H)

[Formula 2-2]

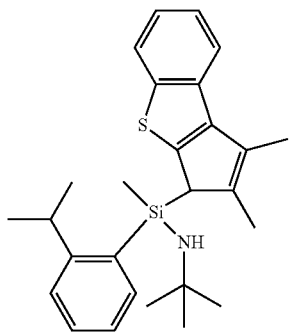

Synthesis of N-tert-butyl-1-(1,2-dimethyl-3H-benzo[b]cyclopenta[d]thiophene-3-yl)-1,1-(2-isopropylphenyl)(methyl)silaneamine Preparation of chloro-1-(1,2-dimethyl-3H-benzo[b]cyclopenta[d]thiophene-3-yl)-1,1-(2-isopropylphenyl)(methyl)silane To a 100 ml schlenk flask, 3 g (1 eq, 14.98 mmol) of 1,2-dimethyl-3H-benzo[b]cyclopenta[d]thiophene and 30 ml of THF were added, and 6.3 ml (1.05 eq, 14.98 mmol, 2.5 M in hexane) of n-BuLi was added thereto dropwisely at −30° C., followed by stirring at room temperature overnight. The THF solution of Li-complex thus stirred was injected into a schlenk flask containing 3.5 g (1.0 eq, 14.98 mmol) of dichloro(2-isopropylphenyl)(methyl)silane and 30 ml of THF at −78° C. by cannulation, followed by stirring at room temperature overnight. After stirring, the reaction mixture was vacuum dried, extracted with 60 ml of hexane, vacuum dried again, and washed with hexane to obtain 6.0 mg of an ivory solid (99%, dr=1:1).

Preparation of N-tert-butyl-1-(1,2-dimethyl-3H-benzo[b]cyclopenta[d]thiophene-3-yl)-1,1-(2-isopropylphenyl)(methyl)silanamine To a 100 ml round-bottom flask, 6.03 g (15.4 mmol) of chloro-1-(1,2-dimethyl-3H-benzo[b]cyclopenta[d]thiophene-3-yl)-1,1-(2-isopropylphenyl)(methyl)silane was weighed and injected, and 50 ml of hexane was injected thereto. At room temperature, tBuNH$_2$ (10 eq, 16.2 ml) was injected, and then reacted at room temperature for 2 days. After finishing the reaction, hexane was removed, and extraction with hexane was performed. After drying solvents, 4.54 mg of a yellow solid was obtained (75.3%).

$^1$H-NMR (CDCl$_3$, 500 MHz): δ 7.98 (t, 2H), 7.68 (d, 1H), 7.50 (t, 3H), 7.29 (t, 2H), 7.26 (d, 2H), 7.23 (d, 1H), 7.21 (d, 1H), 7.08 (t, 3H), 7.00 (t, 1H), 3.73-3.67 (m, 1H), 3.57-3.51 (m, 1H), 3.68 (s, 1H), 3.65 (s, 1H), 2.27 (s, 3H), 2.21 (s, 3H), 2.04 (s, 3H), 1.66 (s, 3H), 1.32-1.22 (m, 12H), 1.07 (s, 9H), 1.02 (s, 9H), 0.17 (s, 3H), 0.09 (s, 3H)

[Formula 2-3]

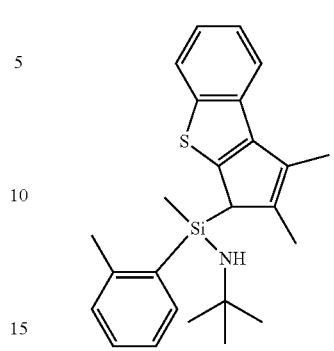

Synthesis of N-tert-butyl-1-(1,2-dimethyl-3H-benzo[b]cyclopenta[d]thiophene-3-yl)-1,1-(methyl)(methylphenyl)silaneamine Preparation of chloro-1-(1,2-dimethyl-3H-benzo[b]cyclopenta[d]thiophene-3-yl)-1,1-(methyl)(2-methylphenyl)silane To a 250 ml schlenk flask, 2.0 g (1.0 eq, 9.985 mmol) of 1,2-dimethyl-3H-benzo[b]cyclopenta[d]thiophene and 50 ml of THF were added, and 4.2 ml (1.05 eq, 10.484 mmol, 2.5 M in hexane) of n-BuLi was added thereto dropwisely at −30° C., followed by stirring at room temperature overnight. The THF solution of Li-complex thus stirred was injected into a schlenk flask containing 2.46 g (1.2 eq, 11.982 mmol) of dichloro(o-tolylmethyl)silane and 30 ml of THF at −78° C. by cannulation, followed by stirring at room temperature overnight. After stirring, the reaction mixture was vacuum dried and extracted with 100 ml of hexane.

Preparation of N-tert-butyl-1-(1,2-dimethyl-3H-benzo[b]cyclopenta[d]thiophene-3-yl)-1,1-(methyl)(2-methylphenyl)silanamine 4.0 g (1.0 eq, 10.0 mmol) of chloro-1-(1,2-dimethyl-3H-benzo[b]cyclopenta[d]thiophene-3-yl)-1,1-(methyl)(2-methylphenyl)silane was stirred in 10 ml of hexane, and 4.2 ml (4.0 eq, 40.0 ml) of tBuNH$_2$ was injected thereto at room temperature, and then stirred at room temperature overnight. After stirring, the reaction mixture was vacuum dried and extracted with 150 ml of hexane. After drying solvents, 4.26 g of a sticky liquid was obtained (99%, dr=1:0.83).

$^1$H-NMR (CDCl$_2$, 500 MHz): δ 7.95 (t, 2H), 7.70 (d, 1H), 7.52 (d, 1H), 7.47-7.44 (m, 2H), 7.24-7.02 (m, 9H), 6.97 (t, 1H), 3.59 (s, 1H), 3.58 (s, 1H), 2.50 (s, 3H), 2.44 (s, 3H), 2.25 (s, 3H), 2.16 (s, 3H), 2.06 (s, 3H), 1.56 (s, 3H), 1.02 (s, 9H), 0.95 (s, 9H), −0.03 (s, 3H), −0.11 (s, 3H)

[Formula 2-4]

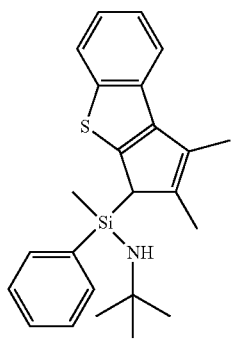

Synthesis of N-tert-butyl-1-(1,2-dimethyl-3H-benzo[b]cyclopenta[d]thiophene-3-yl)-1,1-(methyl)(phenyl)silaneamine Preparation of chloro-1-(1,2-dimethyl-3H-benzo[b]cyclopenta[d]thiophene-3-yl)-1,1-(methyl)(phenyl)silane To a 250 ml schlenk flask, 10 g (1.0 eq, 49.925 mmol) of 1,2-dimethyl-3H-benzo[b]cyclopenta[d]thiophene and 100 ml of THF were added, and 22 ml (1.1 eq, 54.918 mmol, 2.5 M in hexane) of n-BuLi was added thereto dropwisely at −30° C., followed by stirring at room temperature for 3 hours. The THF solution of Li-complex thus stirred was injected into a schlenk flask containing 8.1 ml (1.0 eq, 49.925 mmol) of dichloro(methyl)(phenyl)silane and 70 ml of THF at −78° C. by cannulation, followed by stirring at room temperature overnight. After stirring, the reaction mixture was vacuum dried and extracted with 100 ml of hexane.

Preparation of N-tert-butyl-1-(1,2-dimethyl-3H-benzo[b]cyclopenta[d]thiophene-3-yl)-1,1-(methyl)(phenyl)silanamine To 100 ml of the extracted hexane solution of chloro-1-(1,2-dimethyl-3H-benzo[b]cyclopenta[d]thiophene-3-yl)-1,1-(methyl)(phenyl)silane, 42 ml (8 eq, 399.4 ml) of t-BuNH₂ was injected at room temperature, and then stirred at room temperature overnight. After stirring, the reaction mixture was vacuum dried and extracted with 150 ml of hexane. After drying solvents, 13.36 g of a yellow solid was obtained (68%, dr=1:1).

¹NMR (CDCl₃, 500 MHz): δ 7.93 (t, 2H), 7.79 (d, 1H), 7.71 (d, 1H), 7.60 (d, 2H), 7.48 (d, 2H), 7.40~7.10 (m, 10H, aromatic), 3.62 (s, 1H), 3.60 (s, 1H), 2.28 (s, 6H), 2.09 (s, 3H), 1.76 (s, 3H), 1.12 (s, 18H), 0.23 (s, 3H), 0.13 (s, 3H)

[Formula 2-5]

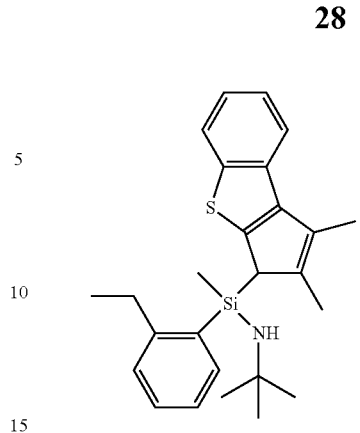

Synthesis of N-tert-butyl-1-(1,2-dimethyl-3H-benzo[b]cyclopenta[d]thiophene-3-yl)-1,1-(2-ethylphenyl)(methyl)silaneamine Preparation of chloro-1-(1,2-dimethyl-3H-benzo[b]cyclopenta[d]thiophene-3-yl)-1,1-(2-ethylphenyl)(methyl)silane To a 100 ml schlenk flask, 2 g (1 eq, 9.99 mmol) of 1,2-dimethyl-3H-benzo[b]cyclopenta[d]thiophene and 50 ml of THF were added, and 4 ml (1 eq, 9.99 mmol, 2.5 M in hexane) of n-BuLi was added thereto dropwisely at −30° C., followed by stirring at room temperature overnight. The THF solution of Li-complex thus stirred was injected into a schlenk flask containing 2.19 ml (1.0 eq, 9.99 mmol) of dichloro(2-ethylphenyl)(methyl)silane and 50 ml of THF at −78° C. by cannulation, followed by stirring at room temperature overnight. After stirring, the reaction mixture was vacuum dried, extracted with 60 ml of hexane, vacuum dried again, and washed with hexane to obtain 3.83 g of an ivory solid (99%, dr=1:1).

Preparation of N-tert-butyl-1-(1,2-dimethyl-3H-benzo[b]cyclopenta[d]thiophene-3-yl)-1,1-(2-ethylphenyl)(methyl)silanamine To a 100 ml round-bottom flask, 3.87 g (10.1 mmol) of chloro-1-(1,2-dimethyl-3H-benzo[b]cyclopenta[d]thiophene-3-yl)-1,1-(2-ethylphenyl)(methyl)silane was weighed and added, and 40 ml of hexane was injected thereto. t-BuNH₂ (10 eq, 10.5 ml) was injected at room temperature, and then reacted at room temperature for 2 days. After finishing the reaction, hexane was removed, and filtering using hexane was performed. After drying solvents, 3.58 g of a yellow solid was obtained (84.4%, dr=1:0.8).

¹H-NMR (CDCl₃, 500 MHz): δ 7.98 (t, 2H), 7.71 (d, 1H), 7.55 (d, 1H), 7.52 (d, 1H), 7.48 (d, 1H), 7.30 (t, 1H), 7.26-7.22 (m, 3H), 7.19 (dd, 2H), 7.12-7.06 (m, 3H), 7.00 (t, 1H), 3.08-2.84 (m, 4H) 3.05-2.84 (m, 2H), 2.28 (s, 3H), 2.20 (s, 3H), 2.08 (s, 3H), 1.62 (s, 3H), 1.26-1.22 (m, 6H), 1.06 (s, 9H), 0.99 (s, 9H), 0.05 (s, 3H), −0.02 (s, 3H)

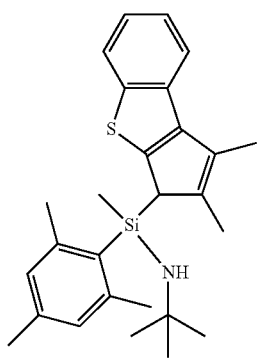

[Formula 2-6]

Synthesis of N-tert-butyl-1-(1,2-dimethyl-3H-benzo[b]cyclopenta[d]thiophene-3-yl)-1,1-(methyl)(2,4,6-trimethylphenyl)silaneamine

Preparation of chloro-1-(1,2-dimethyl-3H-benzo[b]cyclopenta[d]thiophene-3-yl)-1,1-(methyl)(2,4,6-trimethylphenyl)silane To a 100 ml schlenk flask, 1 g (1 eq, 4.99 mmol) of 1,2-dimethyl-3H-benzo[b]cyclopenta[d]thiophene and 30 ml of THF were added, and 2 ml (1 eq, 4.99 mmol, 2.5 M in hexane) of n-BuLi was added thereto dropwisely at −30° C., followed by stirring at room temperature overnight. The THF solution of Li-complex thus stirred was injected into a schlenk flask containing 1.42 ml (1.22 eq, 6.09 mmol) of dichloro(methyl)(2,4,6-trimethylphenyl)silane and 30 ml of THF at −78° C. by cannulation, followed by stirring at room temperature overnight. After stirring, the reaction mixture was vacuum dried, extracted with 60 ml of hexane, vacuum dried again, and washed with hexane to obtain an ivory solid (dr=1:1).

Preparation of N-tert-butyl-1-(1,2-dimethyl-3H-benzo[b]cyclopenta[d]thiophene-3-yl)-1,1-(2-methyl)(2,4,6-trimethylphenyl)silanamine To a 100 ml round-bottom flask, 2.16 g (4.99 mmol) of chloro-1-(1,2-dimethyl-3H-benzo[b]cyclopenta[d]thiophene-3-yl)-1,1-(methyl)(2,4,6-trimethylphenyl)silane was weighed and added, and t-BuNH$_2$ (50 ml) was injected without solvents at room temperature, followed by reacting at room temperature for 2 days. After finishing the reaction, t-BuNH$_2$ was removed, and filtering using hexane was performed. After drying solvents, 2.13 g of a yellow solid was obtained (98.6%, dr=1:0.8).

$^1$H-NMR (CDCl$_3$, 500 MHz): δ 7.99-7.98 (m, 2H), 7.73 (d, 1H), 7.42 (d, 1H), 7.25 (t, 1H), 7.19 (t, 1H), 7.10 (t, 1H), 6.97 (t, 1H), 6.86 (s, 2H), 6.78 (s, 2H), 3.78 (s, 1H), 3.69 (s, 1H), 2.52 (s, 6H), 2.46 (s, 6H), 2.29 (s, 3H), 2.20 (s, 3H), 2.19 (s, 3H), 2.13 (s, 3H), 2.11 (s, 3H), 1.62 (s, 3H), 1.09 (s, 9H), 1.02 (s, 9H), 0.09 (s, 3H), −0.01 (s, 3H)

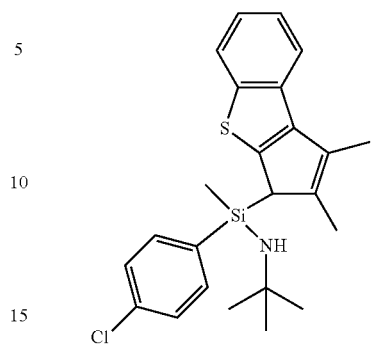

[Formula 2-7]

Synthesis of N-tert-butyl-1-(1,2-dimethyl-3H-benzo[b]cyclopenta[d]thiophene-3-yl)-1,1-(methyl)(4-chlorophenyl)silaneamine

Preparation of chloro-1-(1,2-dimethyl-3H-benzo[b]cyclopenta[d]thiophene-3-yl)-1,1-(methyl)(4-chlorophenyl)silane To a 100 ml schlenk flask, 3 g (1.0 eq, 14.978 mmol) of 1,2-dimethyl-3H-benzo[b]cyclopenta[d]thiophene and 30 ml of THF were added, and 6.6 ml (1.1 eq, 16.475 mmol, 2.5 M in hexane) of n-BuLi was added thereto dropwisely at −30° C., followed by stirring at room temperature overnight. The THF solution of Li-complex thus stirred was injected into a schlenk flask containing 3.38 g (1.0 eq, 14.978 mmol) of dichloro(methyl)(4-chlorophenyl)silane and 30 ml of THF at −78° C. by cannulation, followed by stirring at room temperature overnight. After stirring, the reaction mixture was vacuum dried, extracted with 30 ml of hexane, and vacuum dried again to obtain 5.86 g of an orange sticky solid product (99%, dr=1:1).

Synthesis of N-tert-butyl-1-(1,2-dimethyl-3H-benzo[b]cyclopenta[d]thiophene-3-yl)-1,1-(methyl)(4-chlorophenyl)silanamine To 2 g (1 eq, 5.136 mmol) of the chloro-1-(1,2-dimethyl-3H-benzo[b]cyclopenta[d]thiophene-3-yl)-1,1-(methyl)(4-chlorophenyl)silane thus prepared, 4.3 ml (8 eq, 41.088 mmol) of t-BuNH$_2$ was injected at room temperature, and then stirred at room temperature overnight. After stirring, the reaction mixture was vacuum dried, extracted with 10 ml of toluene, and vacuum dried again to obtain 1.99 g of a yellow sticky solid (91%, dr=1:1).

$^1$H-NMR (CDCl$_2$, 500 MHz): δ 7.95 (d, 2H), 7.79 (d, 1H), 7.73 (d, 1H), 7.75 (d, 4H), 7.35~7.20 (m, 8H), 3.57 (s, 1H), 3.54 (s, 1H), 2.27 (s, 6H), 2.09 (s, 3H), 1.78 (s, 3H), 1.11 (s, 18H), 0.24 (s, 3H), 0.16 (s, 3H)

[Formula 2-8]

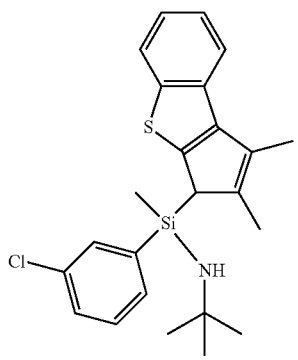

Synthesis of N-tert-butyl-1-(1,2-dimethyl-3H-benzo[b]cyclopenta[d]thiophene-3-yl)-1,1-(methyl)(3-chlorophenyl)silaneamine Preparation of chloro-1-(1,2-dimethyl-3H-benzo[b]cyclopenta[d]thiophene-3-yl)-1,1-(methyl)(3-chlorophenyl)silane To a 100 ml schlenk flask, 3 g (1.0 eq, 14.978 mmol) of 1,2-dimethyl-3H-benzo[b]cyclopenta[d]thiophene and 30 ml of THF were added, and 6.6 ml (1.1 eq, 16.475 mmol, 2.5 M in hexane) of n-BuLi was added thereto dropwisely at −30° C., followed by stirring at room temperature overnight. The THF solution of Li-complex thus stirred was injected into a schlenk flask containing 3.38 g (1.0 eq, 14.978 mmol) of dichloro(methyl)(3-chlorophenyl)silane and 30 ml of THF at −78° C. by cannulation, followed by stirring at room temperature overnight. After stirring, the reaction mixture was vacuum dried, extracted with 30 ml of hexane, and vacuum dried again to obtain 6.00 g of an orange sticky solid product (99%, dr=1:1).

Preparation of N-tert-butyl-1-(1,2-dimethyl-3H-benzo[b]cyclopenta[d]thiophene-3-yl)-1,1-(methyl)(3-chlorophenyl)silanamine To 2 g (1 eq, 5.136 mmol) of chloro-1-(1,2-dimethyl-3H-benzo[b]cyclopenta[d]thiophene-3-yl)-1,1-(methyl)(3-chlorophenyl)silane, 4.3 ml (8 eq, 41.088 mmol) of t-BuNH$_2$ was injected at room temperature, and then stirred at room temperature overnight. After stirring, the reaction mixture was vacuum dried, extracted with 10 ml of toluene, and vacuum dried again to obtain 2.12 g of an orange sticky liquid (97%, dr=1:1).

$^1$H-NMR (CDCl$_3$, 500 MHz): δ 7.93 (t, 2H), 7.79 (d, 1H), 7.73 (d, 1H), 7.52 (s, 1H), 7.44 (d, 1H), 7.38 (s, 1H), 7.35~7.15 (m, 9H), 3.57 (s, 1H), 3.54 (s, 1H), 2.28 (s, 6H), 2.09 (s, 3H), 1.78 (s, 3H), 1.12 (s, 18H), 0.26 (s, 3H), 0.17 (s, 3H)

[Formula 2-9]

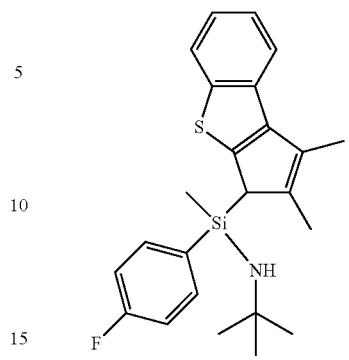

Synthesis of N-tert-butyl-1-(1,2-dimethyl-3H-benzo[b]cyclopenta[d]thiophene-3-yl)-1,1-(methyl)(4-fluorophenyl)silaneamine Preparation of chloro-1-(1,2-dimethyl-3H-benzo[b]cyclopenta[d]thiophene-3-yl)-1,1-(methyl)(4-fluorophenyl)silane To a 100 ml schlenk flask, 2.7 g (1.0 eq, 13.480 mmol) of 1,2-dimethyl-3H-benzo[b]cyclopenta[d]thiophene and 25 ml of THF were added, and 6.0 ml (1.1 eq, 14.828 mmol, 2.5 M in hexane) of n-BuLi was added thereto dropwisely at −30° C., followed by stirring at room temperature overnight. The THF solution of Li-complex thus stirred was injected into a schlenk flask containing 2.82 g (1.0 eq, 13.480 mmol) of dichloro(methyl)(4-fluorophenyl)silane and 25 ml of THF at −78° C. by cannulation, followed by stirring at room temperature overnight. After stirring, the reaction mixture was vacuum dried, extracted with 30 ml of hexane, and vacuum dried again to obtain 3.93 g of an orange sticky liquid product (78%, dr=1:0.85).

Preparation of N-tert-butyl-1-(1,2-dimethyl-3H-benzo[b]cyclopenta[d]thiophene-3-yl)-1,1-(methyl)(4-fluorophenyl)silanamine To 3.93 g (1 eq, 10.543 mmol) of the chloro-1-(1,2-dimethyl-3H-benzo[b]cyclopenta[d]thiophene-3-yl)-1,1-(methyl)(4-fluorophenyl)silane thus prepared, 9 ml (8 eq, 84.344 mmol) of t-BuNH$_2$ was injected at room temperature, and then stirred at room temperature overnight. After stirring, the reaction mixture was vacuum dried, extracted with 30 ml of hexane, and vacuum dried again to obtain 2.71 g of an orange sticky solid (63%, dr=1:0.58).

$^1$H-NMR (CDCl$_3$, 500 MHz): δ 7.92 (d, 2H), 7.79 (d, 1H), 7.72 (d, 1H), 7.55 (t, 2H), 7.39 (t, 2H), 7.35~7.15 (m, 4H), 7.03 (t, 2H), 6.98 (t, 2H), 3.57 (s, 1H), 3.55 (s, 1H), 2.27 (s, 6H), 2.10 (s, 3H), 1.78 (s, 3H), 1.13 (s, 9H), 1.11 (s, 9H), 0.24 (s, 3H), 0.16 (s, 3H)

[Formula 2-10]

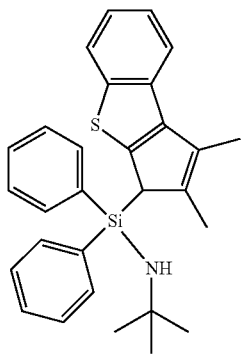

Synthesis of N-tert-butyl-1-(1,2-dimethyl-3H-benzo[b]cyclopenta[d]thiophene-3-yl)-1,1-diphenylsilaneamine Preparation of chloro-1-(1,2-dimethyl-3H-benzo[b]cyclopenta[d]thiophene-3-yl)-1,1-(diphenyl)silane To a 100 ml schlenk flask, 3 g (1.1 eq, 14.978 mmol) of 1,2-dimethyl-3H-benzo[b]cyclopenta[d]thiophene and 30 ml of THF were added, and 6.5 ml (1.2 eq, 16.339 mmol, 2.5 M in hexane) of n-BuLi was added thereto dropwisely at −30° C., followed by stirring at room temperature overnight. The THF solution of Li-complex thus stirred was injected into a schlenk flask containing 2.9 ml (1.0 eq, 13.616 mmol) of dichloro(diphenyl)silane and 30 ml of THF at −78° C. by cannulation, followed by stirring at room temperature overnight. After stirring, the reaction mixture was vacuum dried, extracted with 60 ml of toluene, vacuum dried again and washed with hexane to obtain 3.77 g of an ivory solid (66%).

Preparation of N-tert-butyl-1-(1,2-dimethyl-3H-benzo[b]cyclopenta[d]thiophene-3-yl)-1,1-diphenyl-silanamine To 2 g (1 eq, 4.796 mmol) of the chloro-1-(1,2-dimethyl-3H-benzo[b]cyclopenta[d]thiophene-3-yl)-1,1-(diphenyl)silane thus prepared, 8 ml (16 eq, 76.732 mmol) of t-BuNH$_2$ was injected at room temperature, and then stirred at room temperature overnight. After stirring, the reaction mixture was vacuum dried, extracted with 20 ml of toluene, vacuum dried again and washed with hexane to obtain 2.16 g of an ivory solid (99%).

$^1$H NMR (CDCl$_3$, 500 MHz): δ 7.70 (t, 2H), 7.53 (d, 2H), 7.38~7.13 (m, 10H), 4.02 (s, 1H), 2.05 (s, 3H), 2.00 (s, 3H), 1.12 (s, 9H)

Preparation of Transition Metal Compound

Example 1

Preparation of Compound of Formula 1-1

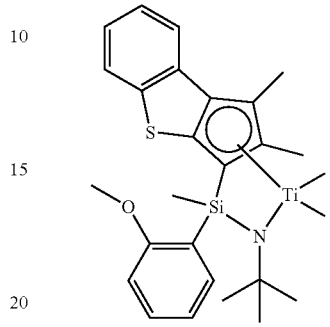

Under a glove box, the ligand compound of Formula 2-1 (467 mg, 1.1 mmol/1.0 eq) and 5.5 ml (0.2 M) of toluene were added to a 50 ml vial, and stirred first. n-BuLi (0.924 ml, 2.31 mmol/2.1 eq, 2.5 M in hexane) was added thereto at −40° C., and then reacted at room temperature overnight. Then, MeMgBr (1.1 ml, 3.3 mmol/3 eq, 3.0 M in diethyl ether) was slowly added thereto dropwisely at −40° C., and TiCl$_4$DME (0.307 mg, 1.1 mmol/1.0 eq) was added in order, followed by stirring at room temperature overnight. After drying solvents, the reaction mixture was filtered using hexane. Then, to a filtrate, DME (0.343 ml, 3.3 mmol/3 eq) was added and stirred at room temperature overnight. After drying solvents, filtering was performed using hexane to obtain 144 mg of a yellow solid (26%, dr=1:1).

$^1$H-NMR (CDCl$_3$, 500 MHz): δ 7.79 (d, 1H), 7.74 (d, 1H), 7.55 (d, 1H), 7.39 (d, 1H), 7.32 (d, 1H), 7.20 (d, 1H), 7.18 (d, 1H), 7.12-7.04 (m, 5H), 7.00 (t, 1H), 6.97 (t, 1H), 6.93 (t, 1H), 6.53 (d, 1H), 3.38 (S, 3H), 2.25 (s, 3H), 2.25 (s, 3H), 2.02 (s, 3H), 1.77 (s, 3H), 1.69 (s, 9H), 1.68 (s, 9H), 1.53 (s, 3H), 1.22 (s, 6H), 1.04 (s, 6H), 0.86 (s, 3H), 0.02 (s, 3H)

Example 2

Preparation of Compound of Formula 1-2

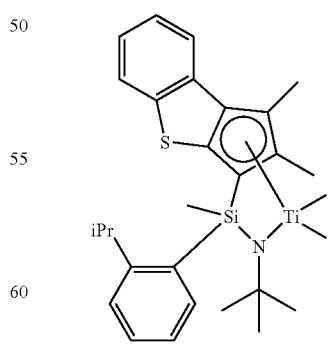

To a 250 ml round-bottom flask, the ligand compound of Formula 2-2 (4.2 g, 10.8 mmol/1.0 eq) and 54 ml (0.2 M) of toluene were added and stirred. n-BuLi (4.3 ml, 9.1 mmol/2.1 eq, 2.5 M in hexane) was added thereto at −40° C., and then stirred at room temperature overnight. Then, MeMgBr (10.8 ml, 32.4 mmol/3.0 eq, 3.0 M in diethyl ether) was slowly added thereto dropwisely at −40° C., and TiCl₄DME (3 g, 10.8 mmol/1 eq) was added in order, followed by stirring at room temperature overnight. Then, the reaction mixture was filtered using hexane.

To a filtrate, DME (5.6 ml, 54 mmol/5 eq) was added and the solution thus obtained was filtered in hexane and concentrated to obtain 1.1 g of a yellow solid (20%, dr=1:0.9).

¹H NMR (CDCl₃, 500 MHz): δ 7.88 (d, 1H), 7.83 (d, 1H), 7.74 (d, 1H), 7.70 (d, 1H), 7.39 (d, 2H), 7.34 (d, 1H), 7.23 (m, 3H), 7.17 (d, 1H), 7.12 (d, 1H), 7.07 (d, 1H), 7.04 (d, 1H), 7.00 (t, 1H), 6.86 (t, 1H), 3.58-3.48 (m, 2H), 2.32 (s, 3H), 2.22 (s, 3H), 1.97 (s, 3H), 1.69 (s, 9H), 1.68 (s, 9H), 1.43 (s, 3H), 1.40 (d, 3H), 1.31 (d, 3H), 1.25 (d, 6H), 1.13 (s, 3H), 0.88 (t, 3H), 0.85 (s, 3H), 0.72 (s, 3H), 0.19 (s, 3H), 0.01 (s, 3H)

Example 3

Synthesis of Compound of Formula 1-3

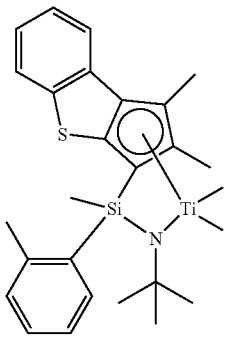

To a 250 ml round-bottom flask, the ligand compound of Formula 2-3 (4.26 g, 10.501 mmol) and 53 ml (0.2 M) of MTBE were added and stirred. n-BuLi (8.6 ml, 21.52 mmol, 2.05 eq, 2.5 M in hexane) was added thereto at −40° C., and then stirred at room temperature overnight.

Then, MeMgBr (8.8 ml, 26.25 mmol, 2.5 eq, 3.0 M in diethyl ether) was slowly added thereto dropwisely at −40° C., and TiCl₄ (10.50 ml, 10.50 mmol) was added in order, followed by stirring at room temperature overnight. Then, the reaction mixture was filtered using hexane.

To a filtrate, DME (3.3 ml, 31.50 mmol) was added and the solution thus obtained was filtered in hexane and concentrated to obtain 3.42 g of a yellow solid (68%, dr=1:0.68).

¹H NMR (CDCl₃, 500 MHz): δ 7.83 (d, 1H), 7.80 (d, 1H), 7.74 (d, 1H), 7.71 (d, 1H), 7.68 (d, 1H), 7.37 (d, 1H), 7.31-6.90 (m, 9H), 6.84 (t, 1H), 2.54 (s, 3H), 2.47 (s, 3H), 2.31 (s, 3H), 2.20 (s, 3H), 1.65 (s, 9H), 1.63 (s, 9H), 1.34 (s, 3H), 1.00 (s, 3H), 0.98 (s, 3H), 0.81 (s, 3H), 0.79 (s, 3H), 0.68 (s, 3H), 0.14 (s, 3H), −0.03 (s, 3H)

Example 4

Preparation of Compound of Formula 1-4

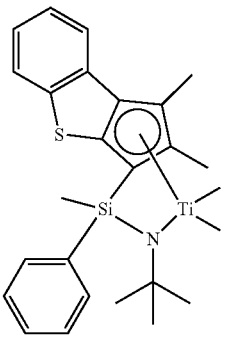

To a 100 ml schlenk flask, 4.93 g (12.575 mmol, 1.0 eq) of the ligand compound of Formula 2-4 and 50 ml (0.2 M) of toluene were added, and 10.3 ml (25.779 mmol, 2.05 eq, 2.5 M in hexane) of n-BuLi was added thereto dropwisely at −30° C., and then stirred at room temperature overnight. After stirring, 12.6 ml (37.725 mmol, 3.0 eq, 3.0 M in diethyl ether) of MeMgBr was added thereto dropwisely, and 13.2 ml (13.204 mmol, 1.05 eq, 1.0 M in toluene) of TiCl₄ was added in order, followed by stirring at room temperature overnight. After stirring, the reaction mixture was vacuum dried and extracted with 150 ml of hexane. After removing solvents to 50 ml, 4 ml (37.725 mmol, 3.0 eq) of DME was added dropwisely and stirred at room temperature overnight. After vacuum drying again, extraction with 150 ml of hexane was performed. After drying solvents, 2.23 g of a brown solid was obtained (38%, dr=1:0.5).

¹H NMR (CDCl₃, 500 MHz): δ 7.98 (d, 1H), 7.94 (d, 1H), 7.71 (t, 6H), 7.50~7.30 (10H), 2.66 (s, 3H), 2.61 (s, 3H), 2.15 (s, 3H), 1.62 (s, 9H), 1.56 (s, 9H), 1.53 (s, 3H), 0.93 (s, 3H), 0.31 (s, 3H), 0.58 (s, 3H), 0.51 (s, 3H), −0.26 (s, 3H), −0.39 (s, 3H)

Example 5

Preparation of Compound of Formula 1-5

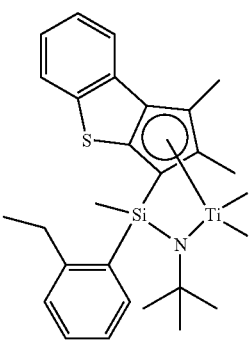

The ligand compound of Formula 2-5 (1.74 g, 4.14 mmol/1.0 eq) and 20.7 ml (0.2 M) of toluene were added to a 50 ml vial and stirred. n-BuLi (3.48 ml, 8.7 mmol/2.1 eq, 2.5 M in hexane) was added thereto at −40° C., and then stirred at room temperature overnight. Then, MeMgBr (4.14 ml, 12.42 mmol/3.0 eq, 3.0 M in diethyl ether) was slowly added thereto dropwisely at −40° C., and TiCl₄DME (1.1 g, 4.14 mmol/1.0 eq) was added in order, followed by stirring at room temperature overnight. After drying solvents, the reaction mixture was filtered using hexane. Then, to a filtrate, DME (1.29 ml, 12.42 mmol/3 eq) was added and stirred at room temperature overnight. After drying solvents, filtering was performed using hexane to obtain 335 mg of a yellow solid (16.3%, dr=1:0.8).

$^1$H NMR (CDCl$_3$, 500 MHz): δ 7.90 (d, 1H), 7.85 (d, 1H), 7.74 (d, 1H), 7.71 (d, 1H), 7.40 (d, 1H), 7.37 (d, 1H), 7.27 (d, 1H), 7.23 (t, 2H), 7.17 (t, 2H), 7.13 (t, 2H), 7.06 (t, 1H), 7.01 (t, 1H), 6.86 (t, 1H), 2.97-2.91 (m, 2H), 2.90-2.82 (m, 2H), 2.33 (s, 3H), 2.22 (s, 3H), 1.96 (s, 3H), 1.68 (s, 9H), 1.66 (s, 9H), 1.38 (s, 3H), 1.32 (t, 3H), 1.24 (t, 3H), 1.07 (s, 3H), 0.88 (s, 3H), 0.85 (s, 3H), 0.72 (s, 3H), 0.19 (s, 3H), 0.01 (s, 3H)

Example 6

Preparation of Compound of Formula 1-6

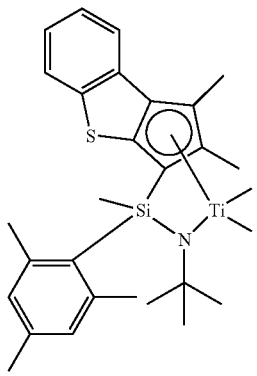

The ligand compound of Formula 2-6 (1.06 g, 2.45 mmol/1.0 eq) and 12.25 ml (0.2 M) of toluene were added to a 50 ml vial and stirred. n-BuLi (2.06 ml, 5.15 mmol/2.1 eq, 2.5 M in hexane) was added thereto at −40° C., and then stirred at room temperature overnight. Then, MeMgBr (2.45 ml, 7.35 mmol/3.0 eq, 3.0 M in diethyl ether) was slowly added thereto dropwisely at −40° C., and TiCl₄DME (686 mg, 2.45 mmol/1.0 eq) was added in order, followed by stirring at room temperature overnight. After drying solvents, the reaction mixture was filtered using hexane. Then, to a filtrate, DME (1.29 ml, 12.42 mmol/3 eq) was added and stirred at room temperature overnight. After drying solvents, filtering was performed using hexane to obtain 400 mg of a yellow solid (32%, dr=1:1).

$^1$H NMR (CDCl$_3$, 500 MHz): δ 7.55 (d, 2H), 7.32 (d, 2h), 7.08 (t, 2H), 6.95 (t, 2H), 6.89 (s, 2H), 6.79 (s, 2H), 2.73 (s, 3H), 2.65 (s, 3H), 2.55 (s, 3H), 2.33 (s, 3H), 2.21 (s, 3H), 2.02 (s, 6H), 1.94 (s, 3H), 1.77 (s, 6H), 1.67 (s, 3H), 1.64 (s, 3H), 1.28 (s, 3H), 1.07 (s, 3H), 1.04 (s, 18H), 0.72 (s, 3H), 0.22 (s, 3H)

Example 7

Preparation of Compound of Formula 1-7

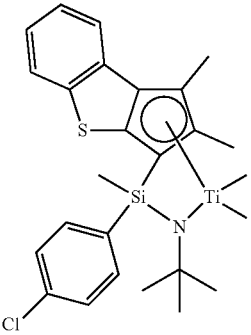

To a 100 ml schlenk flask, 1 g (2.347 mmol, 1.0 eq) of the ligand compound of Formula 2-7 and 10 ml (0.2 M) of toluene were added, and 2.0 ml (4.811 mmol, 2.05 eq, 2.5 M in hexane) of n-BuLi was added thereto dropwisely at −30° C., and then stirred at room temperature overnight. After stirring, 2.4 ml (7.041 mmol, 3.0 eq, 3.0 M in diethyl ether) of MeMgBr was added thereto dropwisely, and 2.5 ml (2.464 mmol, 1.05 eq, 1.0 M in toluene) of TiCl₄ was added in order, followed by stirring at room temperature overnight. After stirring, the reaction mixture was vacuum dried and extracted with 30 ml of hexane. After removing solvents to 10 ml, 1 ml (7.041 mmol, 3.0 eq) of DME was added dropwisely and stirred at room temperature overnight. After vacuum drying again, extraction with 10 ml of hexane was performed. After drying solvents, 0.63 g of a brown solid was obtained (53%, dr=1:0.38).

$^1$H NMR (CDCl$_3$, 500 MHz): δ 7.98 (d, 1H), 7.95 (d, 1H), 7.70 (d, 1H), 7.64 (d, 2H), 7.61 (d, 2H), 7.58 (d, 1H) 7.45~7.30 (m, 8H), 2.66 (s, 3H), 2.61 (s, 3H), 2.14 (s, 3H), 1.59 (s, 3H), 1.55 (s, 9H), 1.54 (s, 9H), 0.83 (s, 3H), 0.80 (s, 3H), 0.58 (s, 3H), 0.52 (s, 3H), −0.25 (s, 3H), −0.37 (s, 3H)

Example 8

Preparation of Compound of Formula 1-8

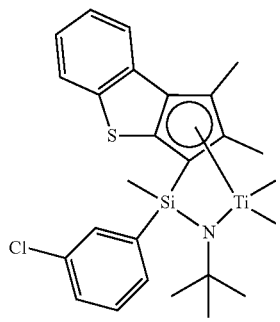

To a 100 ml schlenk flask, 1 g (2.347 mmol, 1.0 eq) of the ligand compound of Formula 2-8 and 10 ml (0.2 M) of toluene were added, and 2.0 ml (4.811 mmol, 2.05 eq, 2.5 M in hexane) of n-BuLi was added thereto dropwisely at −30° C., followed by stirring at room temperature overnight.

After stirring, 2.4 ml (7.041 mmol, 3.0 eq, 3.0 M in diethyl ether) of MeMgBr was added thereto dropwisely, and 2.5 ml (2.464 mmol, 1.05 eq, 1.0 M in toluene) of TiCl₄ was added in order, followed by stirring at room temperature overnight. After stirring, the reaction mixture was vacuum dried and extracted with 30 ml of hexane. After removing solvents to 10 ml, 1 ml (7.041 mmol, 3.0 eq) of DME was added dropwisely and stirred at room temperature overnight. After vacuum drying again, extraction with 10 ml of hexane was performed. After drying solvents, 0.79 g of a brown moist solid was obtained (53%, dr=1:0.35).

$^1$H NMR (CDCl₃, 500 MHz): δ 7.98 (d, 1H), 7.94 (d, 1H), 7.70 (d, 2H), 7.67 (s, 1H), 7.64 (s, 1H), 7.58 (d, 1H), 7.56 (d, 1H), 7.45~7.30 (m, 8H), 2.66 (s, 3H), 2.61 (s, 3H), 2.14 (s, 3H), 1.60 (s, 3H), 1.55 (s, 18H), 0.92 (s, 3H), 0.91 (s, 3H), 0.60 (s, 3H), 0.53 (s, 3H), −0.22 (s, 3H), −0.36 (s, 3H)

Example 9

Preparation of Compound of Formula 1-9

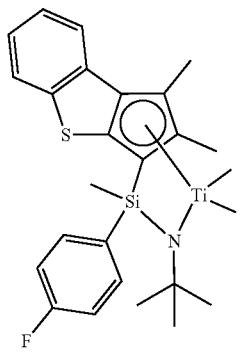

To a 100 ml schlenk flask, 0.56 g (1.371 mmol, 1.0 eq) of the ligand compound of Formula 2-9 and 7 ml (0.2 M) of toluene were added, and 1.2 ml (2.810 mmol, 2.05 eq, 2.5 M in hexane) of n-BuLi was added thereto dropwisely at −30° C., followed by stirring at room temperature overnight. After stirring, 1.4 ml (4.113 mmol, 3.0 eq, 3.0 M in diethyl ether) of MeMgBr was added thereto dropwisely, and 1.4 ml (1.440 mmol, 1.05 eq, 1.0 M in toluene) of TiCl₄ was added in order, followed by stirring at room temperature overnight. After stirring, the reaction mixture was vacuum dried and extracted with 20 ml of hexane. After removing solvents to 10 ml, 0.5 ml (4.113 mmol, 3.0 eq) of DME was added dropwisely and stirred at room temperature overnight. After vacuum drying again, extraction with 20 ml of hexane was performed. After drying solvents, 0.48 g of a red brown solid was obtained (72%, dr=1:0.36).

$^1$H NMR (CDCl₃, 500 MHz): δ 7.98 (d, 1H), 7.95 (d, 1H), 7.65~7.75 (m, 5H), 7.56 (d, 1H), 7.40 (t, 2H), 7.38~7.10 (m, 6H), 2.70 (s, 3H), 2.66 (s, 3H), 2.14 (s, 3H), 1.60 (s, 3H), 1.54 (s, 18H), 0.92 (s, 3H), 0.90 (s, 3H), 0.58 (s, 3H), 0.52 (s, 3H), −0.25 (s, 3H), −0.38 (s, 3H)

Example 10

Preparation of Compound of Formula 1-10

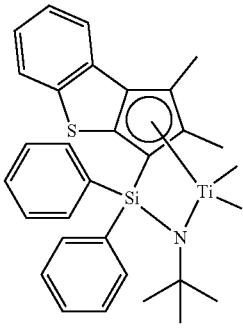

To a 100 ml schlenk flask, 0.6 g (1.322 mmol, 1.0 eq) of the ligand compound of Formula 2-10 and 8 ml (0.2 M) of toluene were added, and 1.1 ml (2.711 mmol, 2.05 eq, 2.5 M in hexane) of n-BuLi was added thereto dropwisely at −30° C., followed by stirring at room temperature overnight. After stirring, 1.4 ml (3.967 mmol, 3.0 eq, 3.0 M in diethyl ether) of MeMgBr was added thereto dropwisely, and 1.4 ml (1.322 mmol, 1.0 eq, 1.0 M in toluene) of TiCl₄ was added in order, followed by stirring at room temperature overnight. After stirring, the reaction mixture was vacuum dried and extracted with 40 ml of hexane. After removing solvents to 10 ml, 0.4 ml (3.967 mmol, 3.0 eq) of DME was added dropwisely and stirred at room temperature overnight. After vacuum drying again, extraction with 10 ml of hexane was performed. After drying solvents, 0.5 g of a yellow solid was obtained (72%, dr=1:1).

$^1$H NMR (CDCl₃, 500 MHz): δ 7.98 (d, 1H), 7.79 (d, 2H), 7.76 (d, 2H), 7.55 (d, 1H), 7.50 (d, 1H), 7.44~7.35 (m, 6H), 7.25 (t, 1H), 2.66 (s, 3H), 1.75 (s, 3H), 1.72 (s, 9H), 0.60 (s, 3H), −0.26 (s, 3H)

Comparative Example 1

Preparation of Ligand Compound

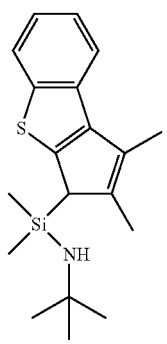

[Formula 11]

Synthesis of N-tert-butyl-1-(1,2-dimethyl-3H-benzo [b]cyclopenta[d]thiophene-3-yl)-1,1-dimethylsilaneamine To a 100 ml schlenk flask, 4.65 g (15.88 mmol) of chloro-1-(1,2-dimethyl-3H-benzo[b]cyclopenta[d]thiophene-3-yl)-1,1-dimethylsilane was weighed and added, and 80 ml of THF was added thereto. At room temperature, tBuNH$_2$ (4 eq, 6.68 mmol) was added thereto, followed by reacting at room temperature for 3 days. After finishing the reaction, THF was removed, and filtering using hexane was performed. After drying solvents, 4.50 g of a yellow liquid was obtained (86%).

$^1$H-NMR (in CDCl$_3$, 500 MHz): 7.99 (d, 1H), 7.83 (d, 1H), 7.35 (dd, 1H), 7.24 (dd, 1H), 3.49 (s, 1H), 2.37 (s, 3H), 2.17 (s, 3H), 1.27 (s, 9H), 0.19 (s, 3H), −0.17 (s, 3H)

[Formula 11-1]

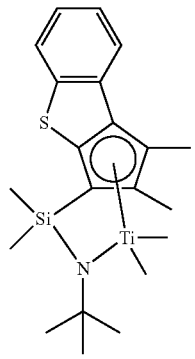

To a 50 ml schlenk flask, N-tert-butyl-1-(1,2-dimethyl-3H-benzo[b]cyclopenta[d]thiophene-3-yl)-1,1-dimethylsilaneamine (1.06 g, 3.22 mmol/1.0 eq) and 16.0 ml (0.2 M) of MTBE were added and stirred first. n-BuLi (2.64 ml, 6.60 mmol/2.05 eq, 2.5 M in THF) was added thereto at −40° C., and then stirred at room temperature overnight. Then, MeMgBr (2.68 ml, 8.05 mmol/2.5 eq, 3.0 M in diethyl ether) was slowly added thereto dropwisely at −40° C., and TiCl$_4$ (2.68 ml, 3.22 mmol/1.0 eq, 1.0 M in toluene) was added in order, followed by stirring at room temperature overnight. Then, the reaction mixture was filtered by passing through Celite using hexane. After drying solvents, 1.07 g of a brown solid was obtained (82%).

$^1$H-NMR (CDCl$_3$, 500 MHz): δ 7.99 (d, 1H), 7.68 (d, 1H), 7.40 (dd, 1H), 7.30 (dd, 1H), 3.22 (s, 1H), 2.67 (s, 3H), 2.05 (s, 3H), 1.54 (s, 9H), 0.58 (s, 3H), 0.57 (s, 3H), 0.40 (s, 3H), −0.45 (s, 3H)

Preparation Example of Polymers

Experimental Examples 1 to 10, and Comparative Experimental Examples 1 to 4

To a 2 L autoclave reactor, a hexane solvent (1.0 L) and 1-octene (in an amount shown in Table 1 below) were added, and the reactor was pre-heated to 150° C. At the same time, the pressure of the reactor was charged with ethylene (35 bars) in advance. A dimethylanilinium tetrakis(pentafluorophenyl) borate (AB) cocatalyst (9 μmol) and a compound (3 μmol) of the third column in Table 1 below, which was treated with a triisobutylaluminum (Tibal) compound (0.25 mmol) were injected to the reactor in order by applying argon with high pressure. Then, a copolymerization reaction was performed for 8 minutes. After that, the remaining ethylene gas was exhausted out, and a polymer solution was added to an excessive amount of ethanol to induce precipitation. The precipitated polymer was washed with ethanol twice or three times, and dried in a vacuum oven at 90° C. for 12 hours or more, and the physical properties thereof were measured.

Various polymers were prepared in accordance with the polymerization temperature, a main catalyst and a catalyst listed in Table 1 below, and the results are shown in Table 1 below.

Evaluation of Physical Properties

Melt Index of Polymer

The melt index (MI) of each polymer was measured according to ASTM D-1238 (condition E, 190° C., 2.16 kg load)

Melting Temperature of Polymer

The melting temperature (Tm) of each polymer was obtained using a differential scanning calorimeter 6000 (DSC) manufactured by PerkinElmer Co, and the melting temperature of a polymer may be measured as follows. About 0.5 mg to 10 mg of each specimen was charged in a container for measurement, and a nitrogen gas flow rate was controlled to 20 ml/min. In order to synchronize the thermal hysteresis of a polyolefin resin, the temperature of each specimen was increased from 0° C. to 150° C. with a rate of 20° C./min, decreased from 150° C. to −100° C. with a rate of 10° C./min and then, increased from −100° C. to 150° C. with a rate of 10° C./min, and the temperature of the peak of a heating curve on heat flow measured by DSC, that is, heat absorption peak during heating was set as the melting temperature.

Density of Polymer

The density of each polymer was obtained by manufacturing a sheet having a thickness of 3 mm and a radius of 2 cm using a press mold at 190° C., annealing thereof at room temperature for 24 hours, and conducting measurement using a Mettler balance.

Measurement of Availability of a Product Having Low Density and High Molecular Weight in Accordance with Temperature

TABLE 1

| Cat. | 1-octene injection amount (ml) | Cat. (compound) | Polymerization temp (° C.) | Cocat | Density (g/cc) | Melt index (MI) (g/10 min) | Tm (° C.) |
|---|---|---|---|---|---|---|---|
| Comparative Experimental Example 1 | 140 | Formula 11-1 (Comparative Example 1) | 150 | AB | 0.888 | 0.6 | — |
| Experimental Example 1 | 140 | Formula 1-1 (Example 1) | 150 | AB | 0.884 | 0.2 | — |

TABLE 1-continued

| Cat. | 1-octene injection amount (ml) | Cat. (compound) | Polymerization temp (° C.) | Cocat | Density (g/cc) | Melt index (MI) (g/10 min) | Tm (° C.) |
|---|---|---|---|---|---|---|---|
| Comparative Experimental Example 2 | 310 | Formula 11-1 (Comparative Example 1) | 150 | AB | 0.871 | 2.7 | (56.9)/ 66.8 |
| Experimental Example 2 | 310 | Formula 1-2 (Example 2) | 150 | AB | 0.865 | 3.2 | (47.8)/ 62.1 |
| Experimental Example 3 | 310 | Formula 1-3 (Example 3) | 150 | AB | 0.866 | 2.6 | (49.8)/ 61.8 |
| Experimental Example 4 | 310 | Formula 1-4 (Example 4) | 150 | AB | 0.866 | 1.4 | (43.0)/ 60.3 |
| Comparative Experimental Example 3 | 330 | Formula 11-1 (Comparative Example 1) | 150 | AB | 0.873 | 7.9 | (60.5)/ 68.7 |
| Experimental Example 5 | 280 | Formula 1-5 (Example 5) | 150 | AB | 0.868 | 1.0 | (52.5)/ 62.3 |
| Experimental Example 6 | 280 | Formula 1-6 (Example 6) | 150 | AB | 0.865 | 1.9 | 23.3/ 54.4 |
| Comparative Experimental Example 4 | 270 | Formula 11-1 (Comparative Example 1) | 150 | AB | 0.879 | 4.1 | 74.0 |
| Experimental Example 7 | 270 | Formula 1-7 (Example 7) | 150 | AB | 0.870 | 2.9 | 64.0 |
| Experimental Example 8 | 270 | Formula 1-8 (Example 8) | 150 | AB | 0.872 | 2.2 | 64.0 |
| Experimental Example 9 | 270 | Formula 1-9 (Example 9) | 150 | AB | 0.867 | 2.5 | — |
| Experimental Example 10 | 260 | Formula 1-10 (Example 10) | 150 | AB | 0.873 | 1.4 | 64.1 |

AB: dimethylanilinium tetrakis(pentafluorophenyl) borate cocatalyst

As verified in Table 1, if the compounds of Examples 1 to 10 were used as the catalysts, polymers having lower density could be prepared when compared to a case where the compound of Comparative Example 1 was used as the catalyst, if the injection amount of 1-octene were the same. In addition, irrespective of the injection amount of 1-octene, a certain trend was shown.

Meanwhile, if the compounds of Examples 1 to 10 were used as the catalysts, low density and low melt index (MI) were shown, and the preparation of a polymer having high molecular weight could be secured.

Accordingly, if a polymer is prepared using the transition metal compounds prepared in Examples 1 to 10 of the present invention, excellent copolymerization degree could be achieved, and a polymer in a low density region and a polymer having high molecular weight could be prepared.

The invention claimed is:

1. A transition metal compound represented by the following Formula 1:

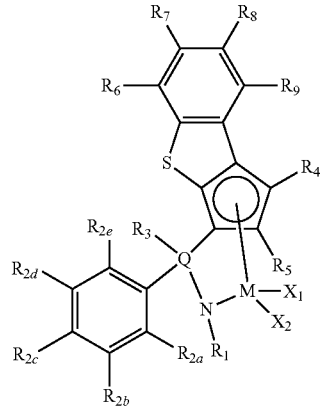

[Formula 1]

in Formula 1, $R_1$ is hydrogen, alkyl having 1 to 20 carbon atoms, cycloalkyl having 3 to 20 carbon atoms, alkenyl having 2 to 20 carbon atoms, alkoxy having 1 to 20 carbon atoms, aryl having 6 to 20 carbon atoms, arylalkoxy having 7 to 20 carbon atoms, alkylaryl having 7 to 20 carbon atoms, or arylalkyl having 7 to 20 carbon atoms;

$R_{2a}$ to $R_{2e}$ are each independently hydrogen, halogen, alkyl having 1 to 20 carbon atoms, cycloalkyl having 3 to 20 carbon atoms, alkenyl having 2 to 20 carbon atoms, alkoxy having 1 to 20 carbon atoms, or aryl having 6 to 20 carbon atoms;

$R_3$ is hydrogen, halogen, alkyl having 1 to 20 carbon atoms, cycloalkyl having 3 to 20 carbon atoms, alkenyl having 2 to 20 carbon atoms, aryl having 6 to 20 carbon atoms, alkylaryl having 6 to 20 carbon atoms, arylalkyl having 7 to 20 carbon atoms, alkyl amido having 1 to 20 carbon atoms, aryl amido having 6 to 20 carbon atoms, alkylidene having 1 to 20 carbon atoms, or phenyl which is substituted with one or more selected from the group consisting of halogen, alkyl having 1 to 20 carbon atoms, cycloalkyl having 3 to 20 carbon atoms, alkenyl having 2 to 20 carbon atoms, alkoxy having 1 to 20 carbon atoms and aryl having 6 to 20 carbon atoms;

$R_4$ to $R_9$ are each independently hydrogen, silyl, alkyl having 1 to 20 carbon atoms, cycloalkyl having 3 to 20 carbon atoms, alkenyl having 2 to 20 carbon atoms, aryl having 6 to 20 carbon atoms, alkylaryl having 7 to 20 carbon atoms, arylalkyl having 7 to 20 carbon atoms, or a metalloid radical of a metal in group 14 which is substituted with hydrocarbyl having 1 to 20 carbon atoms;

wherein adjacent two or more of $R_6$ to $R_9$ are optionally connected to form a ring, Q is Si, C, N, P or S;

M is a transition metal in group 4; and $X_1$ and $X_2$ are each independently hydrogen, halogen, alkyl having 1 to 20 carbon atoms, cycloalkyl having 3 to 20 carbon atoms, alkenyl having 2 to 20 carbon atoms, aryl having 6 to 20 carbon atoms, alkylaryl having 7 to 20 carbon atoms, arylalkyl having 7 to 20 carbon atoms, alkylamino having 1 to 20 carbon atoms, arylamino having 6 to 20 carbon atoms, or alkylidene having 1 to 20 carbon atoms.

2. The transition metal compound of claim 1, wherein
$R_1$ is hydrogen, alkyl having 1 to 20 carbon atoms, cycloalkyl having 3 to 20 carbon atoms, alkoxy having 1 to 20 carbon atoms, aryl having 6 to 20 carbon atoms, arylalkoxy having 7 to 20 carbon atoms, alkylaryl having 7 to 20 carbon atoms, or arylalkyl having 7 to 20 carbon atoms;

$R_{2a}$ to $R_{2e}$ are each independently hydrogen, halogen, alkyl having 1 to 12 carbon atoms, cycloalkyl having 3 to 12 carbon atoms, alkenyl having 2 to 12 carbon atoms, alkoxy having 1 to 12 carbon atoms, or phenyl;

$R_3$ is hydrogen, halogen, alkyl having 1 to 12 carbon atoms, cycloalkyl having 3 to 12 carbon atoms, alkenyl having 2 to 12 carbon atoms, aryl having 6 to 20 carbon atoms, alkylaryl having 7 to 13 carbon atoms, arylalkyl having 7 to 13 carbon atoms, or phenyl which is substituted with one or more selected from the group consisting of halogen, alkyl having 1 to 12 carbon atoms, cycloalkyl having 3 to 12 carbon atoms, alkenyl having 2 to 12 carbon atoms, alkoxy having 1 to 12 carbon atoms and phenyl;

$R_4$ to $R_9$ are each independently hydrogen, alkyl having 1 to 20 carbon atoms, cycloalkyl having 3 to 20 carbon atoms, aryl having 6 to 20 carbon atoms, alkylaryl having 7 to 20 carbon atoms, or arylalkyl having 7 to 20 carbon atoms;

wherein adjacent two or more of $R_6$ to $R_9$ are optionally connected to form an aliphatic ring having 5 to 20 carbon atoms or an aromatic ring having 6 to 20 carbon atoms; wherein the aliphatic ring or the aromatic ring is optionally substituted with halogen, alkyl having 1 to 20 carbon atoms, alkenyl having 2 to 12 carbon atoms, or aryl having 6 to 12 carbon atoms;

Q is Si;
M is Ti: and
$X_1$ and $X_2$ are each independently hydrogen, halogen, alkyl having 1 to 12 carbon atoms, cycloalkyl having 3 to 12 carbon atoms, alkenyl having 2 to 12 carbon atoms, aryl having 6 to 12 carbon atoms, alkylaryl having 7 to 13 carbon atoms, arylalkyl having 7 to 13 carbon atoms, alkylamino having 1 to 13 carbon atoms, or arylamino having 6 to 12 carbon atoms.

3. The transition metal compound of claim 1, wherein
$R_1$ is hydrogen, alkyl having 1 to 12 carbon atoms, cycloalkyl having 3 to 12 carbon atoms, alkoxy having 1 to 12 carbon atoms, aryl having 6 to 12 carbon atoms, arylalkoxy having 7 to 13 carbon atoms, alkylaryl having 7 to 13 carbon atoms, or arylalkyl having 7 to 13 carbon atoms;

$R_{2a}$ to $R_{2e}$ are each independently hydrogen, halogen, alkyl having 1 to 12 carbon atoms, cycloalkyl having 3 to 12 carbon atoms, alkenyl having 2 to 12 carbon atoms, alkoxy having 1 to 12 carbon atoms, or phenyl;

$R_3$ is hydrogen, halogen, alkyl having 1 to 12 carbon atoms, cycloalkyl having 3 to 12 carbon atoms, alkenyl having 2 to 12 carbon atoms, alkylaryl having 7 to 13 carbon atoms, arylalkyl having 7 to 13 carbon atoms, phenyl, or phenyl which is substituted with one or more selected from the group consisting of halogen, alkyl having 1 to 12 carbon atoms, cycloalkyl having 3 to 12 carbon atoms, alkenyl having 2 to 12 carbon atoms, alkoxy having 1 to 12 carbon atoms and phenyl;

$R_4$ to $R_9$ are each independently hydrogen, alkyl having 1 to 12 carbon atoms, cycloalkyl having 3 to 12 carbon atoms, aryl having 6 to 12 carbon atoms, alkylaryl having 7 to 13 carbon atoms, or arylalkyl having 7 to 13 carbon atoms;

wherein adjacent two or more of $R_6$ to $R_9$ are optionally connected to form an aliphatic ring having 5 to 12 carbon atoms or an aromatic ring having 6 to 12 carbon atoms; wherein the aliphatic ring or the aromatic ring is optionally substituted with halogen, alkyl having 1 to 12 carbon atoms, alkenyl having 2 to 12 carbon atoms, or aryl having 6 to 12 carbon atoms, Q is Si;
M is Ti; and
$X_1$ and $X_2$ are each independently hydrogen, halogen, alkyl having 1 to 12 carbon atoms, or alkenyl having 2 to 12 carbon atoms.

4. The transition metal compound of claim 1, wherein
$R_1$ is hydrogen or alkyl having 1 to 12 carbon atoms;
$R_{2a}$ to $R_{2e}$ are each independently hydrogen, halogen, alkyl having 1 to 12 carbon atoms, or alkoxy having 1 to 12 carbon atoms;
$R_3$ is hydrogen, alkyl having 1 to 12 carbon atoms, or phenyl;
$R_4$ and $R_5$ are each independently hydrogen, or alkyl having 1 to 12 carbon atoms;
$R_6$ to $R_9$ are each independently hydrogen or methyl;
Q is Si;
M is Ti; and
$X_1$ and $X_2$ are each independently hydrogen or alkyl having 1 to 12 carbon atoms.

5. The transition metal of claim 1, wherein the compound represented by Formula 1 is a compound represented by one of the following formulae:

[Formula 1-1]

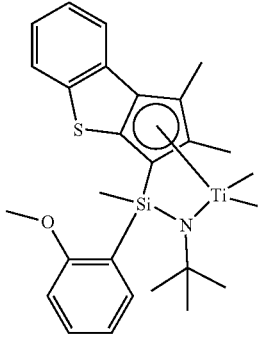

[Formula 1-2]

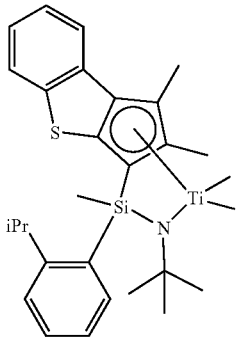

[Formula 1-3]
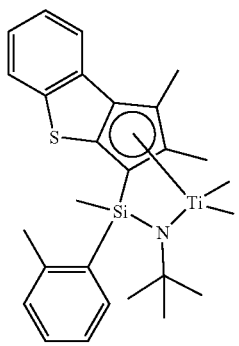
[Formula 1-4]
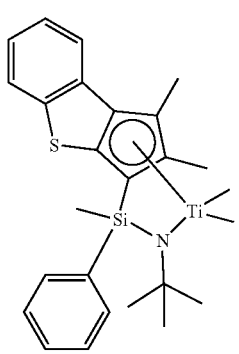
[Formula 1-5]
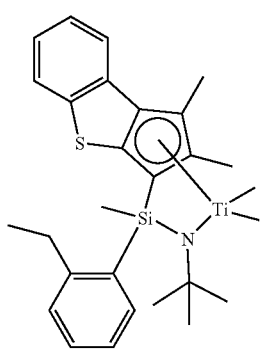
[Formula 1-6]
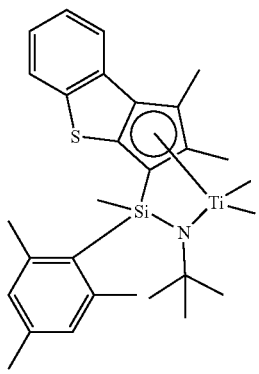
[Formula 1-7]
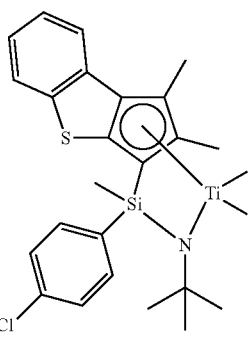
[Formula 1-8]
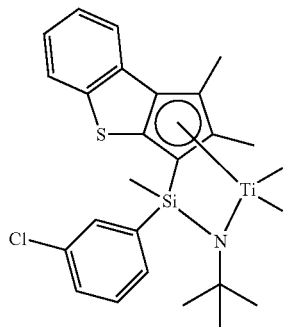
[Formula 1-9]
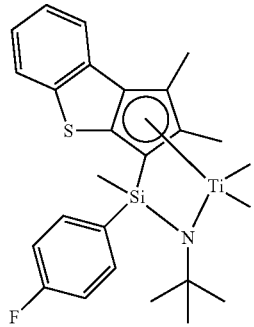
[Formula 1-10]
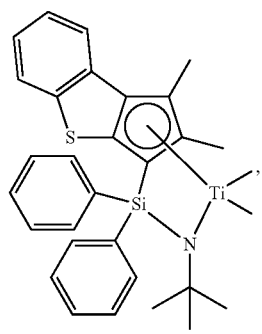

6. A ligand compound represented by the following Formula 2:

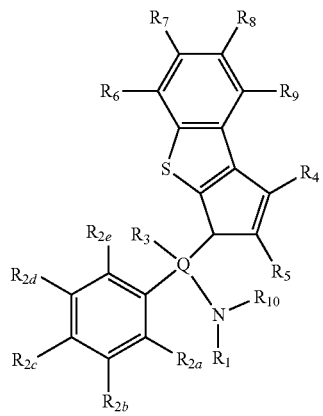

[Formula 2]

in Formula 2, $R_1$, and $R_{10}$ are each independently hydrogen, alkyl having 1 to 20 carbon atoms, cycloalkyl having 3 to 20 carbon atoms, alkenyl having 2 to 20 carbon atoms, alkoxy having 1 to 20 carbon atoms, aryl having 6 to 20 carbon atoms, arylalkoxy having 7 to 20 carbon atoms, alkylaryl having 7 to 20 carbon atoms, or arylalkyl having 7 to 20 carbon atoms;

$R_{2a}$ to $R_{2e}$ are each independently hydrogen, halogen, alkyl having 1 to 20 carbon atoms, cycloalkyl having 3 to 20 carbon atoms, alkenyl having 2 to 20 carbon atoms, alkoxy having 1 to 20 carbon atoms, or aryl having 6 to 20 carbon atoms;

$R_3$ is hydrogen, halogen, alkyl having 1 to 20 carbon atoms, cycloalkyl having 3 to 20 carbon atoms, alkenyl having 2 to 20 carbon atoms, aryl having 6 to 20 carbon atoms, alkylaryl having 6 to 20 carbon atoms, arylalkyl having 7 to 20 carbon atoms, alkyl amido having 1 to 20 carbon atoms, aryl amido having 6 to 20 carbon atoms, alkylidene having 1 to 20 carbon atoms, or phenyl which is substituted with one or more selected from the group consisting of halogen, alkyl having 1 to 20 carbon atoms, cycloalkyl having 3 to 20 carbon atoms, alkenyl having 2 to 20 carbon atoms, alkoxy having 1 to 20 carbon atoms and aryl having 6 to 20 carbon atoms;

$R_4$ to $R_9$ are each independently, hydrogen, silyl, alkyl having 1 to 20 carbon atoms, cycloalkyl having 3 to 20 carbon atoms, alkenyl having 2 to 20 carbon atoms, aryl having 6 to 20 carbon atoms, alkylaryl having 7 to 20 carbon atoms, arylalkyl having 7 to 20 carbon atoms, or a metalloid radical of a metal in group 14, which is substituted with hydrocarbyl having 1 to 20 carbon atoms; wherein adjacent two or more of $R_6$ to $R_9$ are optionally connected to form a ring; and Q is Si, C, N, P or S.

7. The ligand compound of claim 6, wherein $R_1$, $R_{10}$ and $R_{11}$ are each independently hydrogen, alkyl having 1 to 12 carbon atoms, cycloalkyl having 3 to 12 carbon atoms, alkoxy having 1 to 12 carbon atoms, aryl having 6 to 12 carbon atoms, arylalkoxy having 7 to 13 carbon atoms, alkylaryl having 7 to 13 carbon atoms, or arylalkyl having 7 to 13 carbon atoms;

$R_{2a}$ to $R_{2e}$ are each independently hydrogen, halogen, alkyl having 1 to 12 carbon atoms, cycloalkyl having 3 to 12 carbon atoms, alkenyl having 2 to 12 carbon atoms, alkoxy having 1 to 12 carbon atoms, or phenyl;

$R_3$ is hydrogen, halogen, alkyl having 1 to 12 carbon atoms, cycloalkyl having 3 to 12 carbon atoms, alkenyl having 2 to 12 carbon atoms, alkylaryl having 7 to 13 carbon atoms, arylalkyl having 7 to 13 carbon atoms, phenyl, or phenyl which is substituted with one or more selected from the group consisting of halogen, alkyl having 1 to 12 carbon atoms, cycloalkyl having 3 to 12 carbon atoms, alkenyl having 2 to 12 carbon atoms, alkoxy having 1 to 12 carbon atoms and phenyl;

$R_4$ to $R_9$ are each independently, hydrogen, alkyl having 1 to 12 carbon atoms, cycloalkyl having 3 to 12 carbon atoms, aryl having 6 to 12 carbon atoms, alkylaryl having 7 to 13 carbon atoms, or arylalkyl having 7 to 13 carbon atoms;

wherein adjacent two or more of $R_6$ to $R_9$ are optionally connected to form an aliphatic ring having 5 to 12 carbon atoms or an aromatic ring having 6 to 12 carbon atoms; wherein the aliphatic ring or the aromatic ring is optionally substituted with halogen, alkyl having 1 to 12 carbon atoms, alkenyl having 2 to 12 carbon atoms, or aryl having 6 to 12 carbon atoms; and Q is Si.

8. The ligand compound of claim 6, wherein the compound represented by Formula 2 is a compound represented by one of the following formulae:

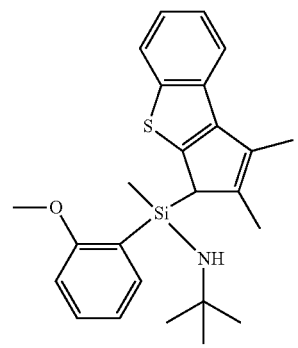

[Formula 2-1]

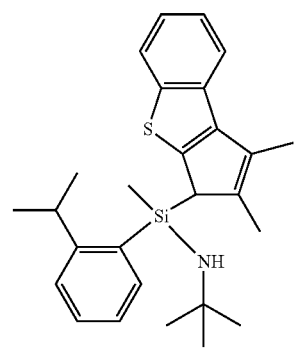

[Formula 2-2]

[Formula 2-3]

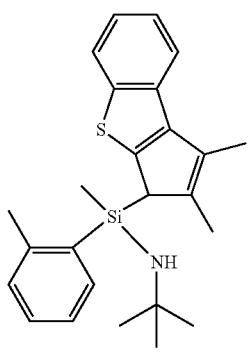

[Formula 2-4]

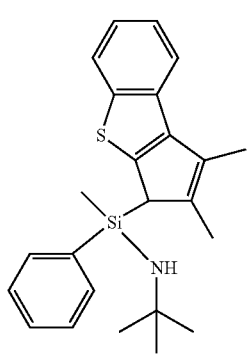

[Formula 2-5]

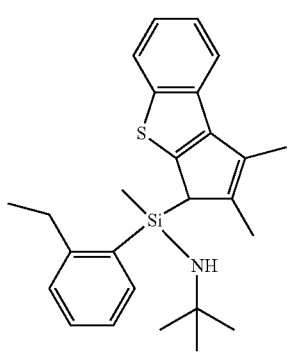

[Formula 2-6]

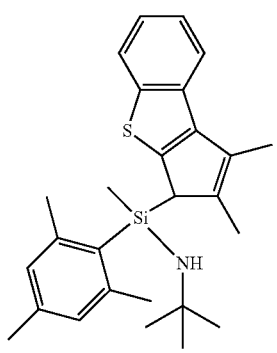

[Formula 2-7]

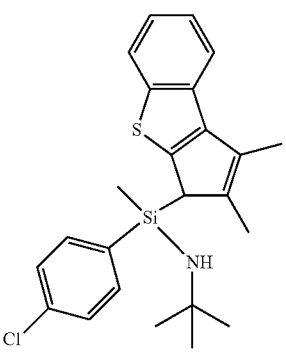

[Formula 2-8]

[Formula 2-9]

[Formula 2-10]

9. A method for preparing the ligand compound according to claim 6, the method comprising:
   a) reacting a compound represented by Formula 4 below with a compound represented by the following Formula 5 below to prepare a compound represented by Formula 3 below; and
   b) reacting the compound represented by Formula 3 with a compound represented by Formula 6 below to prepare the ligand compound represented by Formula 2:

[Formula 4]

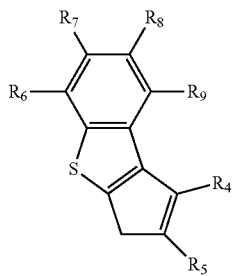

[Formula 5]

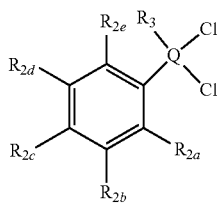

[Formula 3]

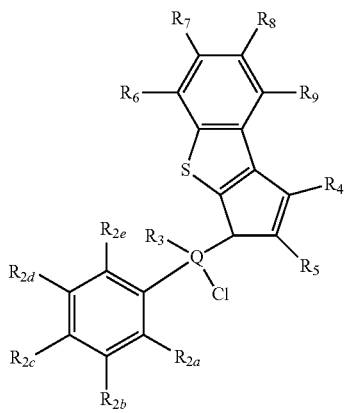

[Formula 6]

$R_1R_{10}NH$ in the above formulae, $R_1$ and $R_{10}$, $R_{2a}$ to $R_{2e}$, and Q are the same as defined in Formula 2.

10. A method for preparing the transition metal compound according to claim 1, by reacting a compound represented by Formula 2 below with a compound represented by Formula 7 below and an organolithium compound:

[Formula 2]

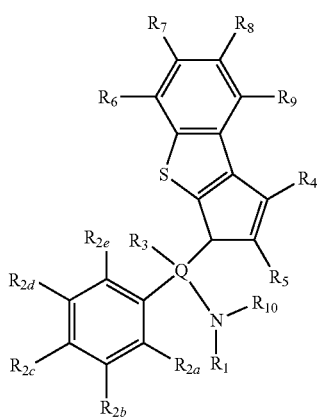

[Formula 7]

$M(X_1X_2)_2$ in the above formulae, $R_{10}$ is hydrogen, alkyl having 1 to 20 carbon atoms, cycloalkyl having 3 to 20 carbon atoms, alkenyl having 2 to 20 carbon atoms, alkoxy having 1 to 20 carbon atoms, aryl having 6 to 20 carbon atoms, arylalkoxy having 7 to 20 carbon atoms, alkylaryl having 7 to 20 carbon atoms, or arylalkyl having 7 to 20 carbon atoms; and $R_1$ to $R_9$, $R_{2a}$ to $R_{2e}$, Q, M, $X_1$, and $X_2$ are the same as defined in Formula 1.

11. A catalyst composition comprising the transition metal compound according to claim 1, wherein the catalyst composition is a polyethylene polymerization catalyst.

12. The catalyst composition of claim 11, which further comprises one or more cocatalysts.

13. The catalyst composition of claim 12, wherein the cocatalyst comprises one or more compounds selected from the following Formulae 8 to 10:

$$-[Al(R_{13})-O]_a-[ \qquad \text{Formula 8}$$

where each $R_{13}$ is independently a halogen radical, a hydrocarbyl radical of 1 to 20 carbon atoms, or a halogen substituted hydrocarbyl radical of 1 to 20 carbon atoms, and a is an integer of 2 or more;

$$D(R_{13})_3 \qquad \text{[Formula 9]}$$

where D is aluminum or boron, and each $R_{13}$ is independently a halogen radical, a hydrocarbyl radical of 1 to 20 carbon atoms, or a halogen substituted hydrocarbyl radical of 1 to 20 carbon atoms, $$[L-H]^+[Z(A)_4]^-$$

or $$[L]^+[Z(A)_4]^- \qquad \text{[Formula 10]}$$

where L is a neutral or a cationic Lewis acid; H is a hydrogen atom; Z is an element in group 13; and each A is independently aryl having 6 to 20 carbon atoms or alkyl having 1 to 20 carbon atoms, where one or more hydrogen atoms is optionally independently substituted with a substituent; wherein the substituent is halogen, hydrocarbyl having 1 to 20 carbon atoms, alkoxy having 1 to 20 carbon atoms, or aryloxy of 6 to 20 carbon atoms.

14. The catalyst composition of claim 12, wherein the catalyst composition further comprises a reaction solvent.

15. A method for preparing a polymer using the catalyst composition according to claim 11, comprising contacting the transition metal compound according to Formula 1 and one or more olefin monomers.

16. The method for preparing a polymer of claim 15, wherein the polymer is a homopolymer or a copolymer of polyolefin.

17. The method for preparing a polymer of claim 15, wherein the polymer has melt index (Mi) of 3.5 g/10 min or less, and a density of less than 0.90 g/cc.

* * * * *